US012758661B2

(12) United States Patent
Henise et al.

(10) Patent No.: US 12,758,661 B2
(45) Date of Patent: Oct. 13, 2026

(54) STEAM STERILIZATION OF HYDROGELS CROSSLINKED BY BETA-ELIMINATIVE LINKERS

(71) Applicant: ProLynx LLC, San Francisco, CA (US)

(72) Inventors: Jeffrey C. Henise, San Francisco, CA (US); Gary W. Ashley, Alameda, CA (US); Brian Yao, Oakland, CA (US)

(73) Assignee: ProLynx LLC, San Francisco, CA (US)

( * ) Notice: Subject to any disclaimer, the term of this patent is extended or adjusted under 35 U.S.C. 154(b) by 878 days.

(21) Appl. No.: 17/631,325

(22) PCT Filed: Aug. 7, 2020

(86) PCT No.: PCT/US2020/045484

§ 371 (c)(1),
(2) Date: Jan. 28, 2022

(87) PCT Pub. No.: WO2021/026494

PCT Pub. Date: Feb. 11, 2021

(65) Prior Publication Data

US 2022/0265873 A1 Aug. 25, 2022

Related U.S. Application Data

(60) Provisional application No. 62/883,982, filed on Aug. 7, 2019.

(51) Int. Cl.

*A61L 2/07* (2006.01)
*A61K 47/69* (2017.01)

(Continued)

(52) U.S. Cl.

CPC ............ *A61L 2/07* (2013.01); *A61K 47/6903* (2017.08); *A61L 2/04* (2013.01); *A61L 2/16* (2013.01);

(Continued)

(58) Field of Classification Search

CPC ............ A61L 2/07; A61L 2/0023; C08J 3/075
See application file for complete search history.

(56) References Cited

U.S. PATENT DOCUMENTS 8,680,315 B2 3/2014 Santi et al.
8,703,907 B2 4/2014 Gary et al.

(Continued)

FOREIGN PATENT DOCUMENTS

CN 107073167 8/2017
CN 107349464 11/2017

(Continued)

OTHER PUBLICATIONS

Henise et al., "Autoclave sterilization of tetra-polyethylene glycol hydrogel biomaterials with β-eliminative crosslinks," Engineering Reports (2020) 9 pages.

(Continued)

*Primary Examiner* — Donald R Spamer
*Assistant Examiner* — Kayla Rose Sarantakos
(74) *Attorney, Agent, or Firm* — MORRISON & FOERSTER LLP

(57) ABSTRACT

Methods for the steam sterilization of hydrogels crosslinked with a beta-eliminative linker without the drawback of significant degradation are provided.

20 Claims, 6 Drawing Sheets

Cleavage of a β-eliminative linker with a $(CH_3)_2SO_2$-N- modulator at pH 4.0, 5.0, or 7.4 at 25 °C or pH 6.2 (-●-), 5.0 (-■-) and 4.0 (-▲-) at 121 °C for eight consecutive autoclave cycles. The buffers, pH at 25 °C and ΔpH/ΔT values used for estimating pH at 121 °C used were: HEPES, pH 7.4, -0.014; acetate, pH 5, -0.0002, and citrate, -0.0024.

(51) Int. Cl.

| | |
|---|---|
| ***A61L 2/04*** | (2006.01) |
| ***A61L 2/16*** | (2006.01) |
| ***C08J 3/075*** | (2006.01) |
| ***C08K 5/3475*** | (2006.01) |
| *A61L 103/05* | (2026.01) |

(52) U.S. Cl.

CPC ............ *C08J 3/075* (2013.01); *C08K 5/3475* (2013.01); *A61L 2103/05* (2026.01)

(56) References Cited

U.S. PATENT DOCUMENTS

| | | | | |
|---|---|---|---|---|
| 8,754,190 | B2 | 6/2014 | Gary et al. | |
| 8,946,405 | B2 | 2/2015 | Gary et al. | |
| 9,387,254 | B2 | 7/2016 | Santi et al. | |
| 9,649,385 | B2 | 5/2017 | Ashley et al. | |
| 10,016,411 | B2 | 7/2018 | Ashley et al. | |
| 10,086,049 | B2 | 10/2018 | Schneider et al. | |
| 10,342,792 | B2 | 7/2019 | Ashley et al. | |
| 10,398,779 | B2 | 9/2019 | Ashley et al. | |
| 10,413,594 | B2 | 9/2019 | Schneider et al. | |
| 11,179,470 | B2 | 11/2021 | Ashley et al. | |
| 11,181,803 | B2 | 11/2021 | Ashley et al. | |
| 11,454,861 | B2 | 9/2022 | Ashley et al. | |
| 11,730,836 | B2 | 8/2023 | Santi et al. | |
| 12,364,771 | B2 | 7/2025 | Ashley et al. | |
| 12,472,261 | B2 | 11/2025 | Fontaine et al. | |
| 12,478,680 | B2 | 11/2025 | Ashley et al. | |
| 2012/0253071 | A1 | 10/2012 | Rau et al. | |
| 2014/0256626 | A1 | 9/2014 | Schneider et al. | |
| 2014/0288190 | A1 * | 9/2014 | Ashley .................... | A61K 9/06<br>523/105 |
| 2015/0202295 | A1 | 7/2015 | Jordan et al. | |
| 2015/0352246 | A1 | 12/2015 | Henise et al. | |
| 2016/0228601 | A1 * | 8/2016 | He .................... | C08G 65/3312 |
| 2017/0312368 | A1 | 11/2017 | Ashley et al. | |
| 2020/0164083 | A1 | 5/2020 | Schneider et al. | |
| 2020/0360545 | A1 | 11/2020 | Hearn et al. | |
| 2022/0193253 | A1 | 6/2022 | Hangasky, III et al. | |
| 2022/0265873 | A1 | 8/2022 | Henise et al. | |
| 2023/0321286 | A1 | 10/2023 | Hearn et al. | |
| 2024/0041982 | A1 | 2/2024 | Schneider et al. | |
| 2024/0082436 | A1 | 3/2024 | Santi et al. | |
| 2024/0181397 | A1 | 6/2024 | Henise et al. | |
| 2025/0312498 | A1 | 10/2025 | Hearn et al. | |
| 2026/0007768 | A1 | 1/2026 | Ashley et al. | |
| 2026/0034120 | A1 | 2/2026 | Santi et al. | |
| 2026/0041680 | A1 | 2/2026 | Santi et al. | |

FOREIGN PATENT DOCUMENTS

| | | | | | |
|---|---|---|---|---|---|
| CN | 107349464 | A | * | 11/2017 | .......... A61L 24/102 |
| JP | 2007068696 | | | 3/2007 | |
| JP | 2007068696 | A | * | 3/2007 | |
| JP | 2014531433 | A | | 11/2014 | |
| JP | 2019511497 | A | | 4/2019 | |
| KR | 20190038368 | | | 4/2019 | |
| WO | WO-2017/161174 | | | 9/2017 | |
| WO | WO-2019/066505 | | | 4/2019 | |
| WO | WO-2019/152672 | | | 8/2019 | |
| WO | WO-2020206358 | A1 | | 10/2020 | |
| WO | WO-2025174913 | A1 | | 8/2025 | |
| WO | WO-2025217310 | A1 | | 10/2025 | |
| WO | WO-2026020143 | A1 | | 1/2026 | |

OTHER PUBLICATIONS

International Search Report for PCT/US20/45484, mailed Dec. 7, 2020, 4 pages.

Galante et al., "Sterilization of hydorgels for biomedical applications: A review," Journal of Biomedical Materials Research Part B: Applied Biomaterials (2017) 106(6):2472-2492.

Yan et al., "Improved synthesis of hyaluronic acid hydrogel and its effect on tissue augmentation," J. Biomater. Appl. (2012) 27(2):179-186.

Chumsae et al., (2014). "Discovery of a chemical modification by citric acid in a recombinant monoclonal antibody," Anal. Chem., 86:8932-6.

Extended European Search Report and Written Opinion received for European Patent Application No. 20849666.1 mailed on Nov. 8, 2024, 10 pages.

Henise et al., (2019). "In Vitro-In Vivo Correlation for the Degradation of Tetra-PEG Hydrogel Microspheres with Tunable β-Eliminative Crosslink Cleavage Rates," Internat. J. Polymer Sci., 2019:9483127, 7 pages.

Partial European Search Report and Written Opinion received for European Patent Application No. 20849666.1 mailed on May 10, 2024, 11 pages.

Reinecke et al., (2011). "Shift of pH-value during thermal treatments in buffer solutions and selected foods," Int. J. Food Properties, 14(4):870-881.

Santi et al., (2012). "Predictable and tunable half-life extension of therapeutic agents by controlled chemical release from macromolecular conjugates," PNAS, 109(16):6211-6216.

Reid et al., (2015). "Analytical and Simulation-Based Models for Drug Release and Gel-Degradation in a Tetra-PEG Hydrogel Drug-Delivery System," Macromolecules, 48:7359-69.

Schneider et al., (2016). "Hydrogel Drug Delivery System Using Self-Cleaving Covalent Linkers for Once-a-Week Administration of Exenatide," Bioconj Chem, 27:1210-5.

* cited by examiner

Cleavage of a β-eliminative linker with a $(CH_3)_2SO_2$-N- modulator at pH 4.0, 5.0, or 7.4 at 25 °C or pH 6.2 (-●-), 5.0 (-■-) and 4.0 (-▲-) at 121 °C for eight consecutive autoclave cycles. The buffers, pH at 25 °C and ΔpH/ΔT values used for estimating pH at 121 °C used were: HEPES, pH 7.4, -0.014; acetate, pH 5, -0.0002, and citrate, -0.0024.

Optical microscopy of amino-hydrogel microspheres after 0, 1, 2, 3, or 4 autoclave cycles.

Dissolution curves for autoclaves amine-MSs with a β-eliminative linker. tRG values are reported in Table 2. Amino-hydrogel microspheres autoclaved in A) pH 4.0 citrate B) pH 4.0 acetate, and C) pH 4.0 phosphate compared to non-autoclaved particles.

Ratio of free amine groups to PEG for amino-hydrogel microspheres ($R^1$ = (N,N-dimethylamino)sulfonyl)) at pH 9.4, after 0-4 autoclave cycles in different buffers

STEAM STERILIZATION OF HYDROGELS CROSSLINKED BY BETA-ELIMINATIVE LINKERS

CROSS-REFERENCE TO RELATED APPLICATIONS

This application is a national stage application under 35 U.S.C. § 371 of International Application No. PCT/US2020/045484, filed internationally on Aug. 7, 2020, which claims priority to U.S. Provisional Application No. 62/883,982, filed on Aug. 7, 2019, the contents of which are incorporated herein by reference in their entireties.

BACKGROUND OF THE INVENTION

Sterilization of degradable polymeric biomaterials presents a formidable challenge. It is essential that any biomaterial used for injection or implants be provided in a sterile form in order to obtain regulatory approval and to safely proceed to clinical use. Infections due to the implantation of medical devices still constitute a major concern in health care. Due to the inherent complexity of biomaterials, however, it is virtually impossible to predict the outcome of sterilization methods and thereby develop a general set of guidelines for achieving adequate sterility. A review of modern sterilization methods for hydrogels has been published (Galante et al., "Sterilization of hydrogels for biomedical applications: a review," *J. Biomedical Materials Res B: App Biomaterials* (2018) 106B: 2472-92).

In the case of hydrogel sterilization, either the polymer backbone or labile crosslinks controlling degradation or both are adversely affected by commonly used sterilization methods. While it may sometimes be possible to sterilize hydrogels using ionizing gamma irradiation in the presence of a protective solvent as disclosed in PCT publication No. WO2011/05140, significant chemical degradation is always problematic, adding to reproducibility and toxicological concerns. The use of elevated temperature may accelerate chemical reactions and result in hydrogel degradation, for example by accelerated hydrolysis of ester bonds.

U.S. Pat. No. 9,649,385 discloses the preparation of hydrogels crosslinked by groups comprising beta-eliminative linkers. Degradation of these gels is controlled by the pH of the medium, and is controlled primarily by the nature of one or more electron-withdrawing modulator groups present in the linker (Santi et al., *Proc. Natl. Acad. Sci.* USA (2012) 109: 6211-6). However, sterilization of such hydrogels has been effected typically using aseptic manufacturing techniques, for example as disclosed in PCT application No. PCT/US2019/016090 filed 31 Jan. 2019. Maintaining aseptic conditions during a multi-step manufacturing process is challenging, however, and the regulatory burden placed on aseptic processes is quite high, adding significant expense. The present invention overcomes these drawbacks.

All documents cited in the present application are incorporated herein by reference.

DISCLOSURE OF THE INVENTION

The invention is directed to a method for the steam sterilization of hydrogels crosslinked with beta-eliminative linkers without the drawback of significant degradation. This is accomplished by providing the hydrogel in a non-reactive buffer, and exposing the buffered hydrogel to a sterilization cycle for sufficient time to sterilize the hydrogel. The pH value of the buffer at the maximum sterilization temperature and time are adjusted to minimize crosslink cleavage during the sterilization cycle.

DESCRIPTION OF THE DRAWINGS

FIG. 3A: pH 4.0 citrate; FIG. 3B: pH 4.0 acetate; and FIG. 3C: pH 4.0 phosphate. The $t_{RG}$ values are reported in Table 2.

MODES OF CARRYING OUT THE INVENTION

Figure 1:
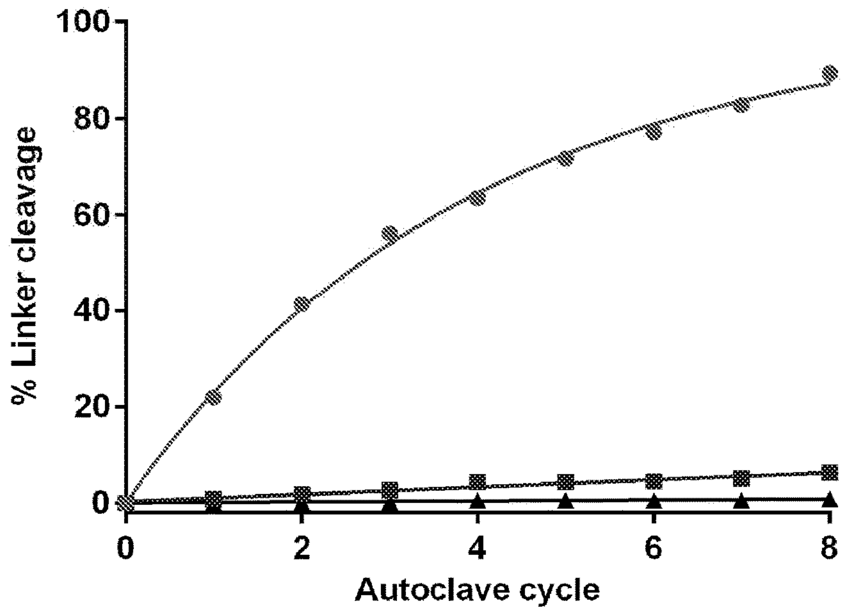
FIG. 1 shows cleavage of a test probe with modulator $R^1$=(N,N-dimethylaminosulfonyl) in different buffers at pH 6.2 (-●-), 5.0 (-■-) and 4.0 (-▲-) at 121 °C for eight consecutive autoclave cycles (20 min hold time). The buffers, pH at 25 °C and ΔpH/ΔT values used for estimating pH at 121 °C used were: HEPES, pH 7.4, −0.014; acetate, pH 5, −0.0002, and citrate, −0.0024.

It has been found that steam sterilization of hydrogels crosslinked with beta-eliminative linkers can be made practical by providing the hydrogel in a non-reactive buffer, and exposing the buffered hydrogel to a sterilization cycle for sufficient time to sterilize the hydrogel. The present inventors have found that by controlling the pH value of the buffer at the maximum sterilization temperature and time, the crosslink cleavage during the sterilization cycle is minimized.

In certain embodiments, the pH of the buffer at maximum sterilization temperature is between pH 2 and pH 5, inclusive, or pH 3 and pH 4. In certain embodiments, the non-reactive buffer is citrate, phosphate or acetate, preferably phosphate or acetate. In certain embodiments, the maximum sterilization temperature is 121 °C and the time at the maximum temperature is less than 1 hour, however these parameters may be adjusted as needed to achieve satisfactory sterilization according to the methods of the invention. In particular embodiments, the buffer is acetate or phosphate at pH 3-4.

Generic structures of PEG hydrogel crosslinked by beta-eliminative linkers and comprising reactive amine groups for subsequent derivatization are shown below. The hydrogels are formed by polymerization of two "prepolymers" as indicated below.

Formula 1
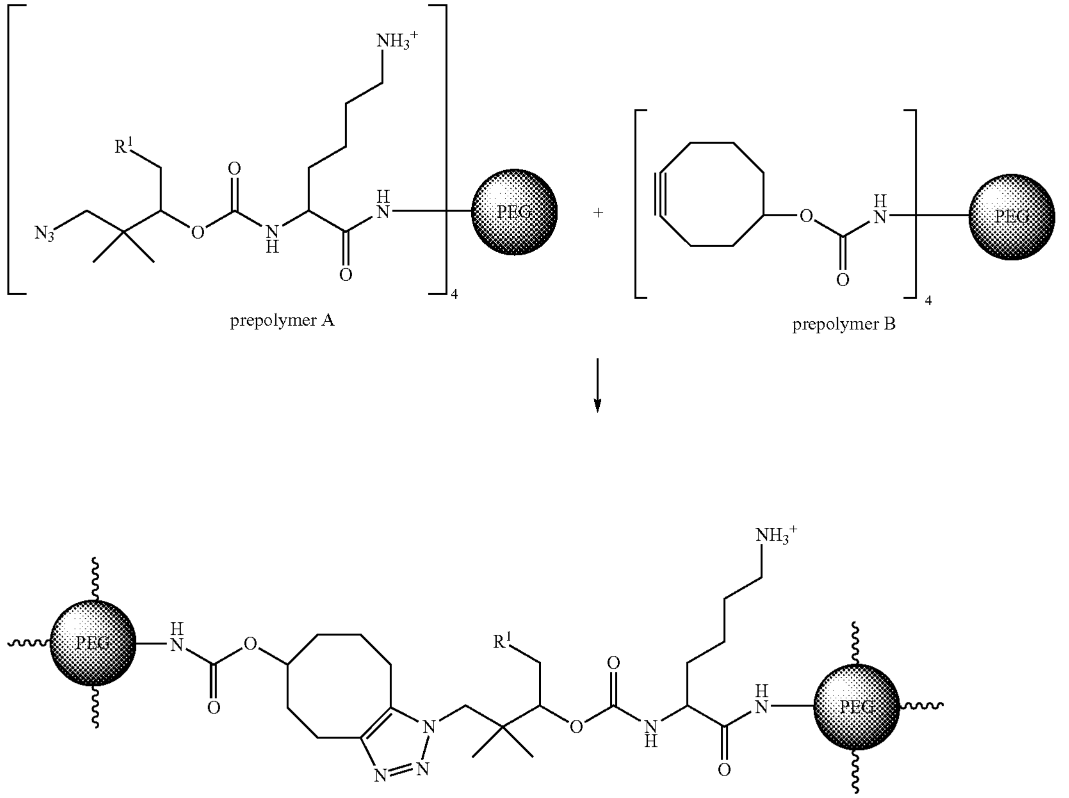
crosslinked hydrogel
Formula 2
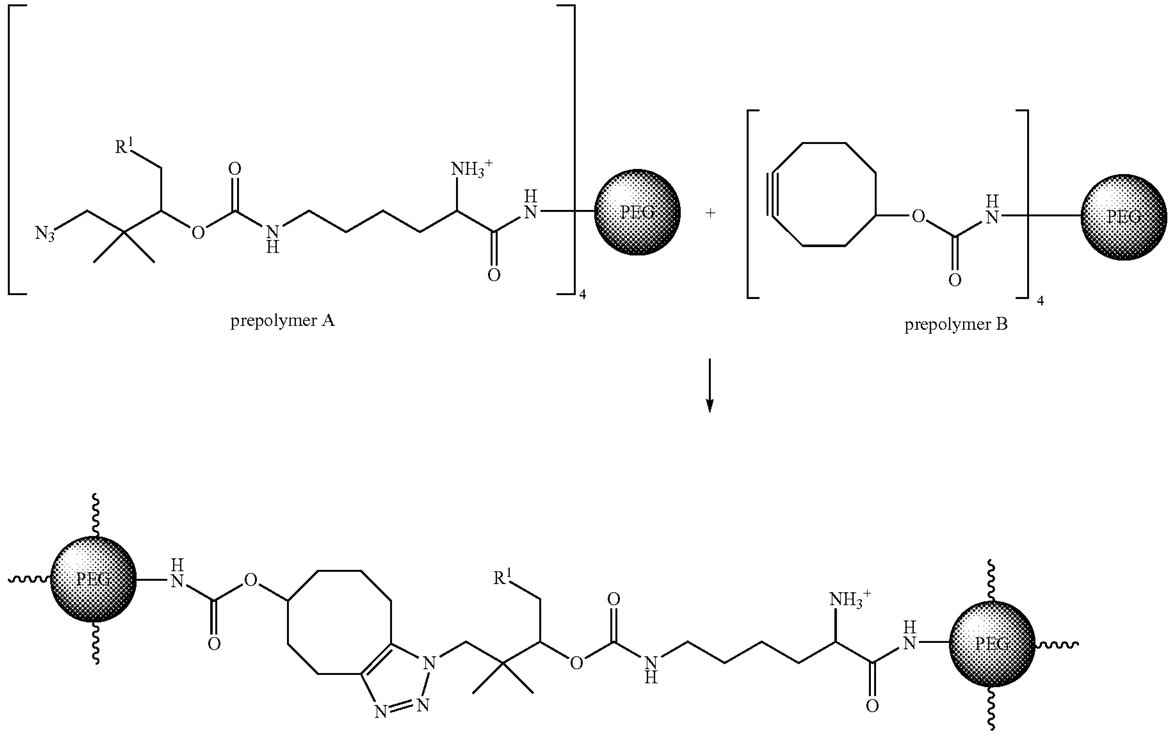
crosslinked hydrogel/linked through lysine ∈-amino In some embodiments of a compound of Formula 1 or Formula 2, $R^1$ is CN; $NO_2$;

optionally substituted aryl;

optionally substituted heteroaryl;

optionally substituted alkenyl;

optionally substituted alkynyl;

$COR^3$ or $SOR^3$ or $SO_2R^3$ wherein $R^3$ is H or optionally substituted alkyl;

aryl or arylalkyl, each optionally substituted;

heteroaryl or heteroarylalkyl, each optionally substituted; or $OR^9$ or $NR^9_2$ wherein each R is independently H or optionally substituted alkyl, or both $R^9$ groups taken together with the nitrogen to which they are attached form a heterocyclic ring;

$SR^4$ wherein $R^4$ is optionally substituted alkyl;

aryl or arylalkyl, each optionally substituted; or heteroaryl or heteroarylalkyl, each optionally substituted.

In some embodiments, $R^1$ is CN or $SO_2R^3$ wherein $R^3$ is H or optionally substituted alkyl; aryl or arylalkyl, each optionally substituted; heteroaryl or heteroarylalkyl, each optionally substituted; or $OR^9$ or $NR^9_2$ wherein each R is independently H or optionally substituted alkyl, or both $R^9$ groups taken together with the nitrogen to which they are attached form a heterocyclic ring. In some embodiments, $R^1$ is CN; $SO_2Me$; $SO_2NMe_2$; $SO_2N(CH_2CH_2)_2X$ or $SO_2(Ph—R^{10})$, wherein X is absent, O, or $CH—R^{10}$ and $R^{10}$ is H, alkyl, alkoxy, $NO_2$, or halogen.

It is understood that the term "alkyl" includes linear, branched, or cyclic saturated hydrocarbon groups of 1-20, 1-12, 1-8, 1-6, or 1-4 carbon atoms. In some embodiment, an alkyl is linear or branched. Examples of linear or branched alkyl groups include, without limitation, methyl, ethyl, n-propyl, isopropyl, n-butyl, t-butyl, isobutyl, sec-butyl, n-pentyl, n-hexyl, n-heptyl, n-octyl, n-nonyl, n-decyl, and the like. In some embodiments, an alkyl is cyclic. Examples of cyclic alkyl groups include, without limitation, cyclopropyl, cyclobutyl, cyclopentyl, cyclopentadienyl, cyclohexyl, and the like.

It is understood that the term "alkoxy" includes alkyl groups bonded to oxygen, including methoxy, ethoxy, isopropoxy, cyclopropoxy, cyclobutoxy, and the like.

It is understood that the term "alkenyl" includes non-aromatic unsaturated hydrocarbons with carbon-carbon double bonds and 2-20, 2-12, 2-8, 2-6, or 2-4 carbon atoms.

It is understood that the term "alkynyl" includes non-aromatic unsaturated hydrocarbons with carbon-carbon triple bonds and 2-20, 2-12, 2-8, 2-6, or 2-4 carbon atoms.

It is understood that the term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and the like.

In some instances, alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

It is understood that the term "halogen" or "halo" includes bromo, fluoro, chloro and iodo.

It is understood that the term "heterocyclic ring" or "heterocyclyl" refers to a 3-15 membered aromatic or non-aromatic ring comprising at least one N, O, or S atom. Examples include, without limitation, piperidinyl, piperazinyl, tetrahydropyranyl, pyrrolidine, and tetrahydrofuranyl, as well as the exemplary groups provided for the term "heteroaryl" above. In some embodiments, a heterocyclic ring or heterocyclyl is non-aromatic. In some embodiments, a heterocyclic ring or heterocyclyl is aromatic.

It is understood that "optionally substituted," unless otherwise specified, means that a group may be unsubstituted or substituted by one or more (e.g., 1, 2, 3, 4 or 5) of the substituents which may be same or different. Examples of substituents include, without limitation, alkyl, alkenyl, alkynyl, halogen, —CN, $—OR^{aa}$, $—SR^{aa}$, $—NR^{aa}R^{bb}$, $—NO_2$, $—C{=}NH(OR^{aa})$, $—C(O)R^{aa}$, $—OC(O)R^{aa}$, $—C(O)OR^{aa}$, $—C(O)NR^{aa}R^{bb}$, $—OC(O)NR^{aa}R^{bb}$, $—NR^{aa}C(O)R^{bb}$, $—NR^{aa}C(O)OR^{bb}$, $—S(O)R^{aa}$, $—S(O)_2R^{aa}$, $—NR^{aa}S(O)R^{bb}$, $—C(O)NR^{aa}S(O)R^{bb}$, $—NR^{aa}S(O)_2R^{bb}$, $—C(O)NR^{aa}S(O)_2R^{bb}$, $—S(O)NR^{aa}R^{bb}$, $—S(O)_2NR^{aa}R^{bb}$, $—P(O)(OR^{aa})(OR^{bb})$, heterocyclyl, heteroaryl, or aryl, wherein the alkyl, alkenyl, alkynyl, cycloalkyl, heterocyclyl, heteroaryl, and aryl are each independently optionally substituted by $R^{cc}$, wherein $R^{aa}$ and $R^{bb}$ are each independently H, alkyl, alkenyl, alkynyl, heterocyclyl, heteroaryl, or aryl, or $R^{aa}$ and $R^{bb}$ are taken together with the nitrogen atom to which they attach to form a heterocyclyl, which is optionally substituted by alkyl, alkenyl, alkynyl, halogen, hydroxyl, alkoxy, or —CN, and wherein:

each $R^{cc}$ is independently alkyl, alkenyl, alkynyl, halogen, heterocyclyl, heteroaryl, aryl, —CN, or $—NO_2$.

For use herein, unless clearly indicated otherwise, use of the terms "a", "an" and the like refers to one or more.

The preparation of hydrogels comprising biodegradable beta-eliminative linkers has been previously disclosed, for example in U.S. Pat. No. 9,649,385, and those further comprising functionalizable amine groups introduced through the use of a lysine spacer have been disclosed, for example in PCT application No. PCT/US2019/016090 filed 31 Jan. 2019 and U.S. Provisional Patent application No. 62/830,280 filed 5 Apr. 2019. While the rate of crosslink cleavage at the beta-eliminative linker is primarily determined be the structure of the group $R^1$ as disclosed in U.S. Pat. No. 8,680,315, the basicity of the amine group to which the linker is attached plays an additional role, such that crosslinks attached via the alpha-amine of lysine cleave more rapidly than those attached via the epsilon-amine for a given $R^1$ under the same reaction conditions. The interplay of these factors allows for the preparation of hydrogels that biodegrade according to predictable and controllable kinetics; see, for example, Henise et al., *Internat. J. Polymer Sci.*, Vol 2019, article ID 9483127.

Various properties of the hydrogel depend upon the extent of crosslinking, and thus the degree to which crosslinks are cleaved during a sterilization process. One such property is the time at which the hydrogel dissolves when placed at a particular pH and temperature, known as the reverse gelation time ($t_{rg}$). The relationship between crosslinking and $t_{rg}$ has been described in Reid et al., *Macromolecules* 2015, 48: 7359-69 as equation (1)

$$t_{rg}=t_{1/2,L2}\cdot ln[(1-f)/0.39]/ln(2) \quad (1)$$

wherein $t_{1/2,L2}$ is the half-life for cleavage of an individual crosslink and f is a hydrogel quality factor, equal to the initial fraction of randomly distributed cleaved crosslinks initially present in the hydrogel. Thus, if crosslinks are cleaved during the sterilization process, the $t_{rg}$ will decrease relative to the initial, unsterilized hydrogel. As illustrated below in Example 3, the extent to which crosslink cleavage during sterilization can be tolerated depends upon the initial quality of the hydrogel and the tolerance within which $t_{rg}$ can vary. The change in $t_{rg}$ of the hydrogel after sterilization is within 20%, preferably within 15%, and more preferably within 10% of the $t_{rg}$ of the hydrogel prior to sterilization.

A further important property of the hydrogel is maintenance of the titer of reactive functional groups after sterilization. Such reactive functional groups may be present so as to allow for subsequent chemical derivatization and attachment of payloads such as drugs or releasable linker-drugs, for example as disclosed in U.S. Pat. No. 9,649,385, PCT application No. PCT/US2019/016090 filed 31 Jan. 2019 and U.S. Provisional Patent application No. 62/830,280 filed 5 Apr. 2019. Such functional groups may show undesirable reactivity towards other portions of the hydrogels or components in the sterilization buffer. Methods for the assay of such functional groups are known in the art, and an example of the assay for when such reactive groups are amines is provided in the examples below.

The following examples illustrate, but do not limit the invention.

Preparation A

PEG-Linker-Lysine Test Probes for Linker Stability ($R^1$=N,N-dimethylsulfonyl or morpholinosulfonyl)

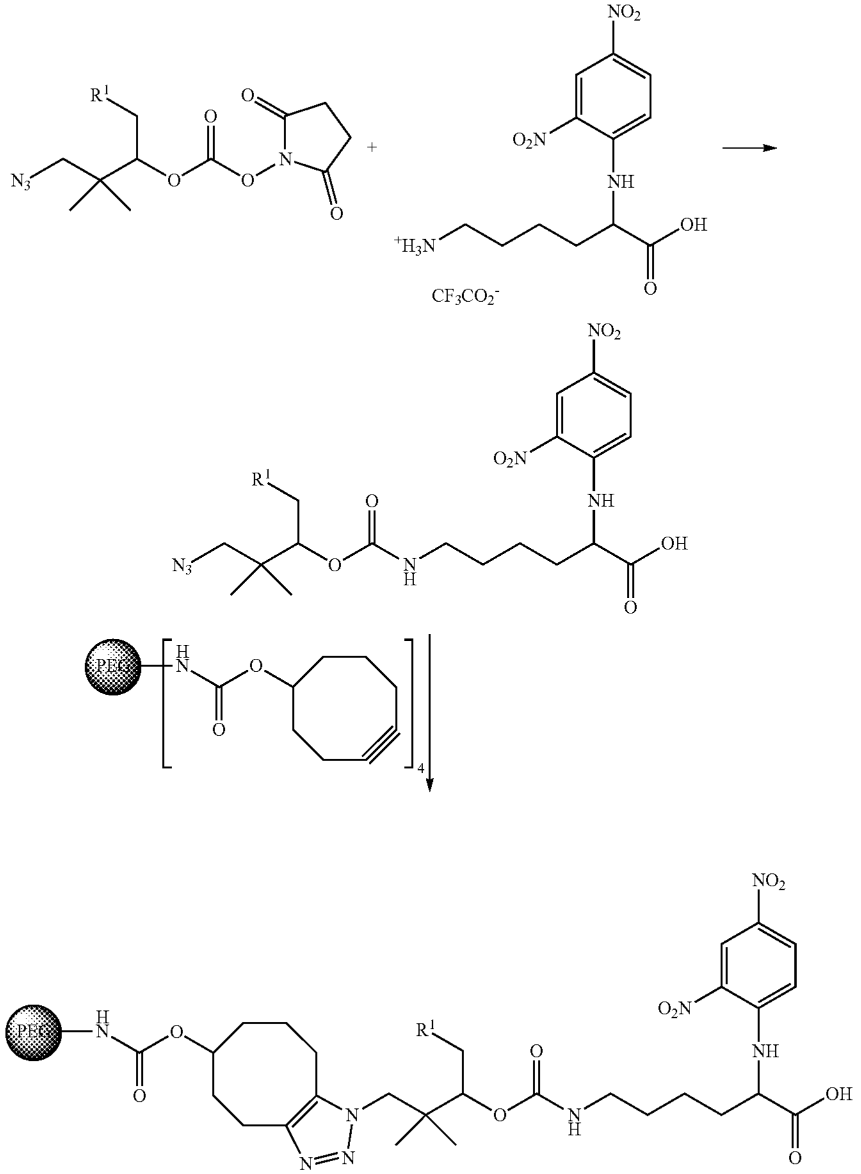

N(α)-(2,4-dinitrophenyl)-N(e)-[(4-azido-3,3-dimethyl-1-(N,N-dimethylaminosulfonyl)-2-butoxycarbonyl)-L-lysine. Prepared according to the general procedures of Santi et al., Proc. Natl. Acad. Sci. USA (2012) 109: 6211-6. A solution of 4-azido-3,3-dimethyl-1-(N,N-dimethylaminosulfonyl)-2-butyl succinimidyl carbonate (40 mg, 100 umol) in 2 mL of MeCN was added to a mixture of N(a)-(2,4-dinitrophenyl)-L-lysine trifluoroacetate salt (50 mg, 120 umol), 0.2 mL of 1 N NaOH, 0.4 mL of 1 M $NaHCO_3$, and 1.4 mL of water. After 10 min, the mixture was acidified with HCl and extracted with EtOAc. The extract was washed with water and brine, dried over $MgSO_4$, filtered, and evaporated to yield the product (59 mg, 100 umol, 100%) as a yellow glass. HPLC gave a single peak; LC-MS showed $[M+H]^+$ m/z 589.1 (calc for $C_{21}H_{33}N_8O_{10}S^+$ m/z 589.2).

Conjugation of N(a)-(2,4-dinitrophenyl)-N(e)-[(4-azido-3,3-dimethyl-1-(N,N-dimethylamino-sulfonyl)-2-butoxy-carbonyl)-L-lysine to $PEG_{10kDa}$-tetracyclooctyne. A solution of the product of Step 1 (11.2 mg, 19 unmol) in 0.2 mL of MeCN was added to a solution of 10-kDa 4-armed PEG-tetracyclooctyne [prepared from 10-kDa PEG-tetraamine and 5-cyclooct-4-ynyl succinimidyl carbonate] (56.6 mM in cyclooctyne, 0.265 mL, 15 umol cyclooctyne) in 20 mM acetate buffer, pH 5.0, and kept at 50 °C for 12 h. The solution was dialyzed (SpectraPor2 membrane, 12-14 kDa cutoff) against methanol to remove unconjugated material, then concentrated to dryness tomprovide the conjugate (43 mg, 90%) which was dissolved in 1 mL of water to provide a stock solution. HPLC indicated free DNP-lysine at <0.1%.

The corresponding conjugate having $R^1$=morpholinosulfonyl was prepared by the same procedure starting with 4-azido-3,3-dimethyl-1-(morpholinosulfonyl)-2-butyl succinimidyl carbonate.

Preparation B

Preparation of amino-hydrogel Microspheres ($R^1$=N,N-dimethylsulfonyl or morpholinosulfonyl)

Amino-hydrogel microspheres were prepared as described in PCT application No. US2019/016090 filed 31 Jan. 2019 (see Example 4) and U.S. Provisional Patent application No. 62/830,280 filed 5 Apr. 2019 (see Example 14), incorporated herein by reference.

In brief, microspheres are formed from prepolymers as shown.

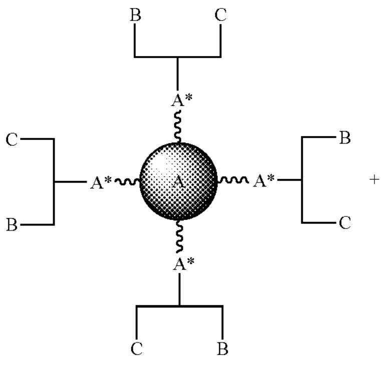

1st prepolymer

-continued

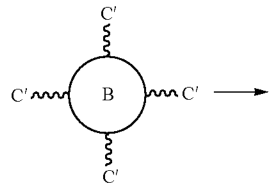

2nd prepolymer

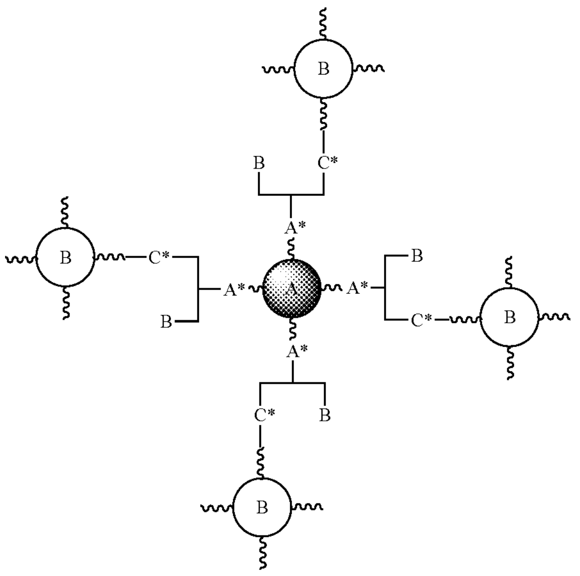

hydrogel

Groups C and C' react to form a connecting functional group, C*. The prepolymer connection to one of C or C' further comprises a cleavable linker introduced by reaction with a molecule such as that of the Formula (3), so as to introduce the cleavable linker into each crosslink of the hydrogel:

(3)

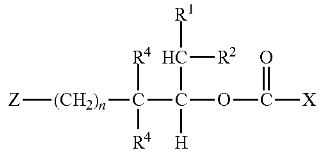

wherein n=0-6, $R^1$ and $R^2$ are independently electron-withdrawing groups, alkyl, or H, and wherein at least one of $R^1$ and $R^2$ is an electron-withdrawing group; each $R^4$ is independently $C_1$-$C_3$ alkyl or taken together may form a 3-6 member ring; X is halogen, active ester such as N-succinimidyloxy, nitrophenoxy, or pentahalophenoxy, or imidazolyl, triazolyl, tetrazolyl, or $N(R^6)CH_2Cl$ wherein $R^6$ is optionally substituted $C_1$-$C_6$ alkyl, optionally substituted aryl, or optionally substituted heteroaryl; and Z is a functional group for connecting the linker to a macromolecular carrier. In some embodiments, n is 1-6. More generally, hydrogels suitable for use in the invention contain crosslinks comprising beta-eliminative linkers of formula (4)

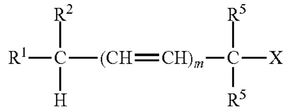

(4)

wherein m is 0 or 1;

X comprises a functional group connecting the crosslinker to a first polymer;

at least one of $R^1$, $R^2$, and $R^5$ comprises a functional group Z connecting the crosslinker to a second polymer;

wherein one and only one of $R^1$ and $R^2$ may be H or may be alkyl, arylalkyl or heteroarylalkyl, each optionally substituted;

at least one or both $R^1$ and $R^2$ is independently CN; $NO_2$;

optionally substituted aryl;

optionally substituted heteroaryl;

optionally substituted alkenyl;

optionally substituted alkynyl;

$COR^3$ or $SOR^3$ or $SO_2R^3$ wherein $R^3$ is H or optionally substituted alkyl;

aryl or arylalkyl, each optionally substituted;

heteroaryl or heteroarylalkyl, each optionally substituted; or $OR^9$ or $NR^9_2$ wherein each R is independently H or optionally substituted alkyl, or both $R^9$ groups taken together with the nitrogen to which they are attached form a heterocyclic ring;

$SR^4$ wherein $R^4$ is optionally substituted alkyl;

aryl or arylalkyl, each optionally substituted; or heteroaryl or heteroarylalkyl, each optionally substituted;

wherein $R^1$ and $R^2$ may be joined to form a 3-8 membered ring; and each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted. X is typically a carbamate O—(C═O)—NH; Z is typically a triazole (resulting from cycloaddition of an azide to an alkyne or cyclooctyne) or a carboxamide or carbamate; however, other options as disclosed in PCT application No. PCT/US2019/016090 filed 31 Jan. 2019 (see Example 4) and U.S. Provisional Patent application No. 62/830,280 filed 5 Apr. 2019 (see Example 14) are also suitable.

In this illustration, a first prepolymer comprises a 4-armed PEG wherein each arm is terminated with an adapter unit having two mutually-unreactive ("orthogonal") functional groups B and C. B and C may be initially present in protected form to allow selective chemistry in subsequent steps. The adapter unit may be a derivative of an amino acid, particularly lysine, cysteine, aspartate, or glutamate, including derivatives wherein the alpha-amine group has been converted to an azide, for example mono-esters of 2-azidoglutaric acid. The adapter unit is connected to each first prepolymer arm through a connecting functional group A*, formed by condensation of a functional group A on each prepolymer arm with cognate functional group A' on the adapter unit. A second prepolymer comprises a 4-armed PEG wherein each arm is terminated with a functional group C' having complimentary reactivity with group C of the first prepolymer, such that crosslinking between the two prepolymers occurs when C and C' react to form C*.

As an illustrative example, H-Lys(Boc)-OH was acylated with a linker of Formula (3) wherein Z=azide to give an adapter unit. This was coupled to 20-kDa 4-armed PEG-tetraamine, and the Boc group removed to provide a first prepolymer wherein A*=amide, B═$NH_2$, and C=azide and wherein the cleavable linker of formula (3) is incorporated into the linkage between each arm and group C of the first prepolymer. The corresponding second prepolymer was prepared by acylation of 20-kDa 4-armed PEG-tetraamine with 5-cyclooctynyl succinimidyl carbonate to give a second prepolymer wherein C'=cyclooctyne. Upon mixing of the first and second prepolymers, reaction of the C=azide and C'=cyclooctyne groups form corresponding triazole groups and thereby crosslink the two prepolymers into a 3-dimensional network, with each crosslink comprising a cleavage linker resulting from incorporation of the compound of Formula (3), and wherein each node resulting from incorporation of a first prepolymer comprises a remaining functional group B═$NH_2$ which can be derivatized for attachment of further linkers, drugs, fluorophores, metal chelators, and the like. Hydrogels of this type have been prepared using PEGs of various sizes, for example 5-, 10-, 20, and 40-kDa. Microsphere suspensions of these hydrogels typically comprise particles of 20-100 um in diameter, although other sizes and physical shapes of the hydrogels can be produced. The stability of the hydrogels under steam sterilization is primarily controlled by the rate of crosslinker cleavage by beta-elimination; as this is dependent on the properties of the linkers and the pH and temperature of the medium but independent of the size and shape of the PEGs or the hydrogel, all such variants of hydrogel structure are suitable for use in the invention.

Example 1

Stability of PEG-Linker-Lysine Test Probes

A. Temperature Dependence of Cleavage Rate

The test probe of Preparation A wherein $R^1$=morpholinosulfonyl was dissolved in 0.1 M phosphate buffer having pH=7.4 at 25 °C (the pH of phosphate buffer is essentially constant over a wide temperature range, see Reinecke et al., *Int. J. Food Properties* (2011) 14:4, 870-881) in an HPLC autosampler vial, then incubated at a set temperature. Aliquots were periodically removed and quenched by addition of 1/10 volume of 1 N HCl, then analyzed by HPLC for released DNP-lysine by HPLC by injecting 10 μL onto a $C_{18}$ column (Phenomenex Jupiter, 300 A, 5 um, 4.6×150 mm), eluting with a linear gradient from 0-100% MeCN/water/0.1% TFA over 10 min and analyzing at 350 nm. Formation of free DNP-lysine was quantitated as % reaction=(AUC DNP-lysine)/[(AUC DNP-lysine)+(AUC conjugate)]×100, where AUC is area under the curve. Reaction rate constants ($h^{-1}$) were then calculated from the slope of ln(% reaction) vs time in hours.

Figure 5:
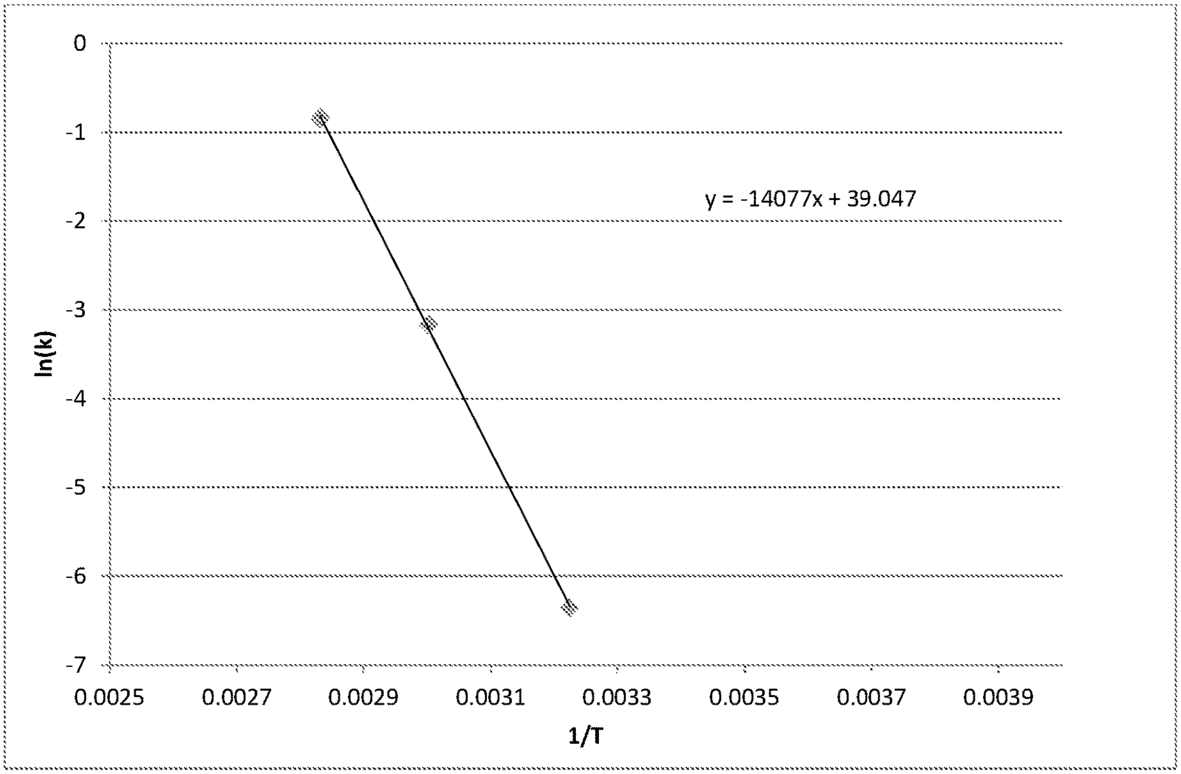
FIG. 5 shows an Arrhenius plot for the cleavage of a beta-eliminative linker between 37° and 80 °C wherein the electron-withdrawing modulator is morpholino-sulfonyl. The data in this plot give the linear relationship ln(k)=39.047-14077/T, wherein k is the rate constant for linker cleavage per hour, and T is the reaction temperature in ° K. These parameters estimate an activation energy $E_a$=117 kJ/mol.
Figure 6:
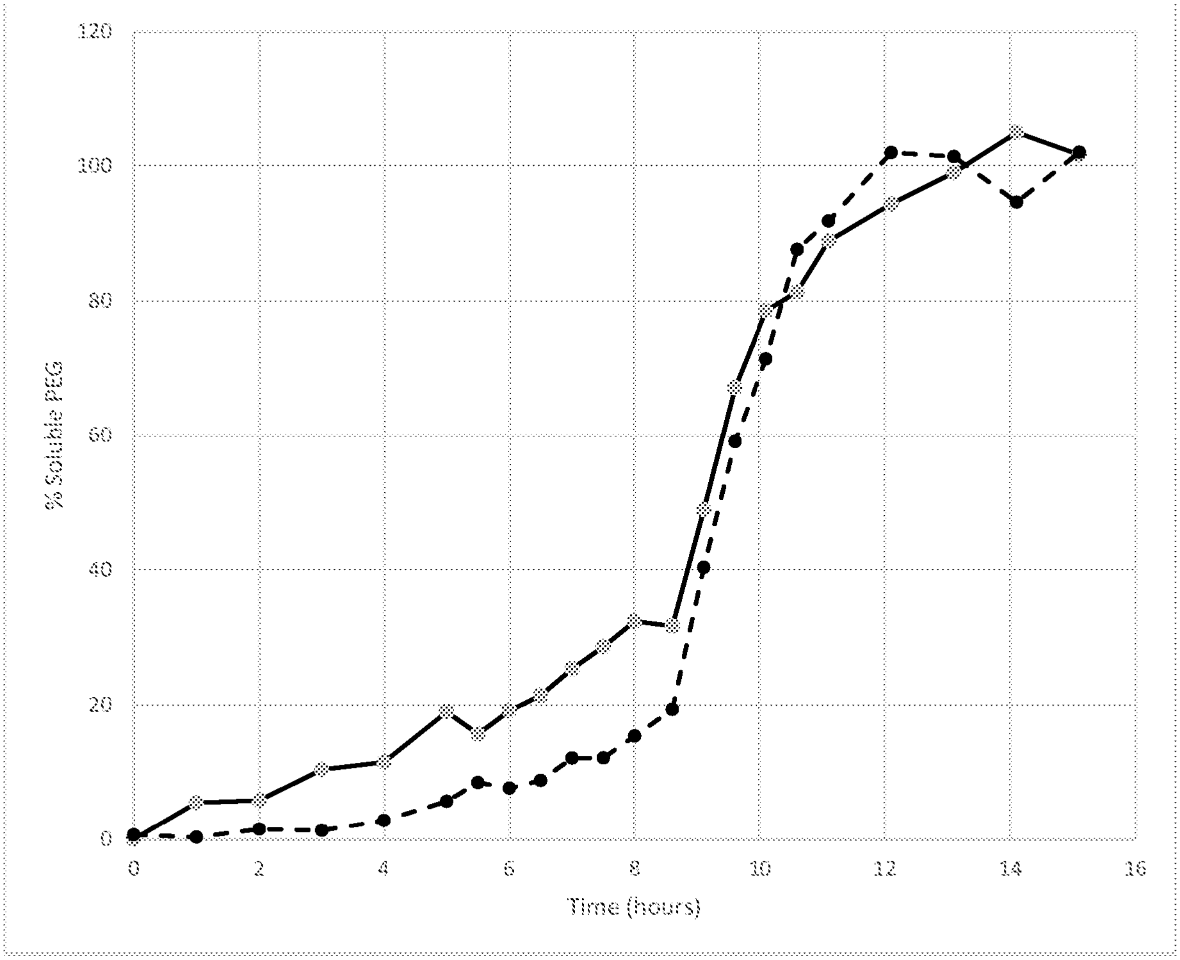
FIG. 6 shows dissolution curves for hydrogel microspheres before and after autoclaving. A hydrogel of Formula 1 was prepared by the reaction of Prepolymer A wherein $R^1$=N,N-dimethylsulfonamide with Prepolymer B, wherein PEG=10-kDa 4-armed PEG in both cases. Samples of the hydrogel microspheres were assayed for dissolution (n=2) by placing in borate buffer, pH 9.4, 37 °C, and assaying periodically for dissolved PEG using the $BaCl_2/I_2/KI$ method. Analysis of the dissolution curves indicates $t_{RG}$=12.0±0.7 h before autoclaving and 11.9±0.7 h after autoclaving. Sterility testing of the autoclaved hydrogel microspheres showed no detectible growth.

Rates were determined at 37, 60, and 80 °C, and then analyzed according to Arrhenius by plotting ln(k) versus 1/T, where T is the reaction temperature in ° K. This provided a linear relationship where ln(k)=39.047−14077/T, thus providing A=9.07×$10^{16}$ $h^{-1}$ and $E_a$=117 kJ/mol, as shown in FIG. 5.

B. Effect of pH

Solutions of the PEG-linker-lysine test probes in buffer were subjected to autoclave cycles, then analyzed by HPLC to measure the extent of linker cleavage by determination of released DNP-lysine. The test probe stocks (0.1 mL) were diluted with 1.0 mL of buffer in a 2-mL screw-cap autosampler vial. Buffers used (and pH at 25 °C) were:

0.125 M HEPES (pH 7.6), 0.1 M citrate (pH 5.0 and 4.0), 0.1 M glycine (pH 2.0).

The vials were sealed and subjected to repeated standard autoclave cycles consisting of (a) evacuation to 5.80 psia; (b) heating to 121 °C with a hold time of 20 min; (c) cooling to 97 °C over ~1.5 h, then allowed to cool to ambient temperature and analyzed. The autoclave temperature was monitored with a probe immersed into 50 mL of water in a 100 mL glass GL45 medium bottle. The autoclave used was a Sterivap model 669 autclave (BMT Medical Technology). Samples were analyzed by HPLC by injecting 10 μL onto a $C_{18}$ column (Phenomenex Jupiter, 300 A, 5 um, 4.6×150 mm), eluting with a linear gradient from 0-100% MeCN/water/0.1% TFA over 10 min and analyzing at 350 nm.

Formation of free DNP-lysine was quantitated as % reaction=(AUC DNP-lysine)/[(AUC DNP-lysine)+(AUC conjugate)]×100. Table 1 gives the observed and estimated amounts of linker cleavage after the first autoclave cycle when $R^1$=(N,N-dimethylamino) sulfonyl.

TABLE 1

Estimated and measured cleavage of a β-eliminative linker with the $SO_2N(CH_3)_2$ modulator at 121° C.

| pH, 25° C. [a] | $t_{1/2}$, 37° C., calc. | pH 121° C. calc. | $t_{1/2}$, 121° C., calc. | % Product/cycle, 121° C., calc. [b] | % Product/cycle, 121° C., obsd. |
|---|---|---|---|---|---|
| 7.6 [A] | 100 d | 6.2 | 4.3 h | 5% | 13% |
| 6.0 | 6.9 y | 5.7 | 13.5 h | 1.7% | 3.8% |
| 5.0 | 69 y | 5.0 | 68 h | 0.3% | 1.9% |
| 4.0 | 690 y | 4.0 | 28 d | ~0% | 0.1% |
| 2.0 | 69,000 y | 2.0 | 7.7 y | ~0 | 0.2% |

[a] pH of buffers was measured at 25° C. and estimated at 121° C. using reported temperature coefficients. The buffers, pH values at 25° C. and ΔpH/ΔT values were Hepes, pH 7.4, −0.014; phosphate, pH 6, −0.0028; phthalate, pH 5, −0.00013; glycine, pH 2, +0.00044;

[b] Calculations use the calculated pH at 121° C.; they do not include the slow cooling period of a cycle and are expected to be lower than observed.

These cumulative results for 8 successive autoclave cycles are shown in FIG. 1. At pH 4.0, the linker cleaved by 0.11% per cycle and were >99% intact after 8 successive cycles. At pH 5.0, the linker cleaved by 0.77% per cycle.

Example 2

Test Autoclave Sterilization of Amino-Hydrogel Microspheres

Sterilization of ~1.5 mL of amino-hydrogel micro spheres of preparation B where $R^1$ is (N,N-dimethylamino)sulfonyl in 2 mL autosampler vials was performed as described in Example 1, then analyzed by microscopy for changes in physical parameters and by time to reverse gelation and by free amine content for changes in chemical structure.

Figure 2:
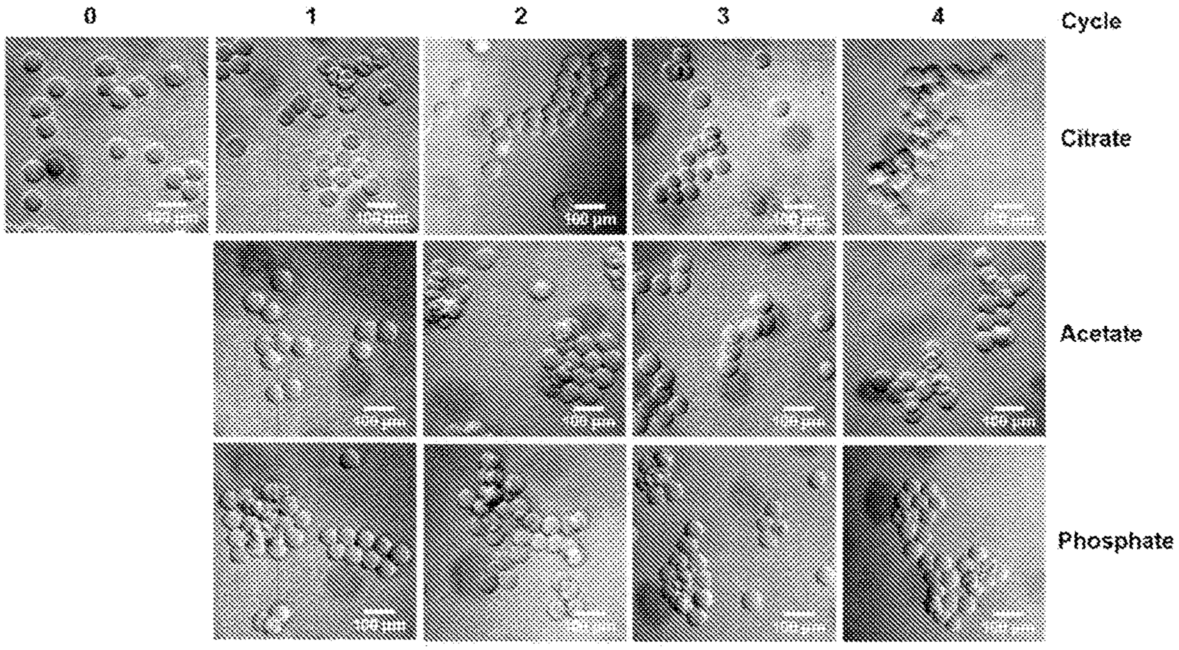
FIG. 2 shows the microscopic morphology of amino-hydrogel microspheres after 0, 1, 2, 3, or 4 autoclave cycles in different buffers.

Visual inspection by optical microscopy indicated no significant changes in microsphere morphology. A 100 mg sample of microsphere slurry was diluted with 0.700 mL 50% DMF/$H_2O$ v/v. A 0.200 mL sample of the mixture was placed on a microscope slide (VWR, 48300-026) and images were collected using a white light microscope (Nikon TMS, SN: 51436) with a 5× objective (Nikon E 4/0.10, 160/—NA) and a monochromatic CCD camera (Unibrain, Fire-I 580b). From three images the particle diameters (N=≥150) were measured using an image analysis software (Image J v 1.52a). The software was calibrated to convert pixels to μm (1.98 μm $pixel^{-1}$) by measurement of an image of a microscope stage micrometer (Electron Microscopy Sciences, 60210-3PG). Depictions of the observed microspheres are shown in FIG. 2.

Results are shown in Table 2.

TABLE 2

Properties of amine-MSs before and after autoclaving at pH 4.

| Buffer | No. cycles | appearance | particle size (μm) [a] | nmol amine/mg PEG [b] | $t_{RG}$, hr |
|---|---|---|---|---|---|
| citrate | 0 | normal | 67 ± 6 | 110 ± 11 | 23 |
| citrate | 1 | normal | 67 ± 4 | 110 ± 30 | 23 |
| | 2 | normal | 65 ± 4 | 94 ± 7 | 25 |
| | 3 | normal | 66 ± 14 | 89 ± 6 | 27 |
| | 4 | normal | 64 ± 4 | 83 ± 17 | 26 |
| acetate | 1 | normal | 69 ± 14 | 120 ± 20 | 25 |
| | 2 | normal | 69 ± 15 | 120 ± 10 | 25 |
| | 3 | normal | 67 ± 11 | 110 ± 4 | 25 |
| | 4 | normal | 65 ± 4 | 110 ± 10 | 23 |
| phosphate | 1 | normal | 64 ± 14 | 120 ± 10 | 25 |
| | 2 | normal | 64 ± 14 | 110 ± 120 | 25 |
| | 3 | normal | 62 ± 13 | 110 ± 10 | 23 |
| | 4 | normal | 59 ± 11 | 110 ± 20 | 26 |

[a] Mean ± SD, >50 microsphere measurements;

[b] Mean ± SD, 4 replicate measurements.

To determine amine and PEG content, a 100 mg aliquot of microsphere slurry was dissolved in 0.900 mL of 50 mM NaOH. The amine content of a 0.060 mL sample of the dissolved MSs was measured using TNBS (2,4,6-trinitrobenzenesulfonic acid solution) as described by Schneider et al., *Bioconj Chem* (2016) 27: 1210. For the PEG assay, a 0.020 mL aliquot of the above dissolved microsphere solution was diluted with 0.980 mL $H_2O$ and acidified with 1.00 mL of 0.5 M $HClO_4$. After transfer of 0.200 mL aliquots to a 96 well microtiter plate, each was treated with a 0.050 mL of 5% w/v mixture of $BaCl_2$ and 0.025 mL of Lugol solution (0.18% w/w $I_2$ and 0.35% w/w KI). After 5 min the $A_{535}$ was measured using a plate reader. The PEG content was determined from a standard curve of $A_{535}$ vs. [PEG] generated from 1.25- to 10 ug $mL^{-1}$ of an 8000 MW linear PEG standard that was pre-calibrated by NMR using a DMF standard (Alvares et al., *Anal. Chem.* (2016) 88: 3730). The ratios of nmol amine/mg PEG of the amino-MSs were calculated using measurements of the free amine and PEG from the same solution.

Figure 3A:
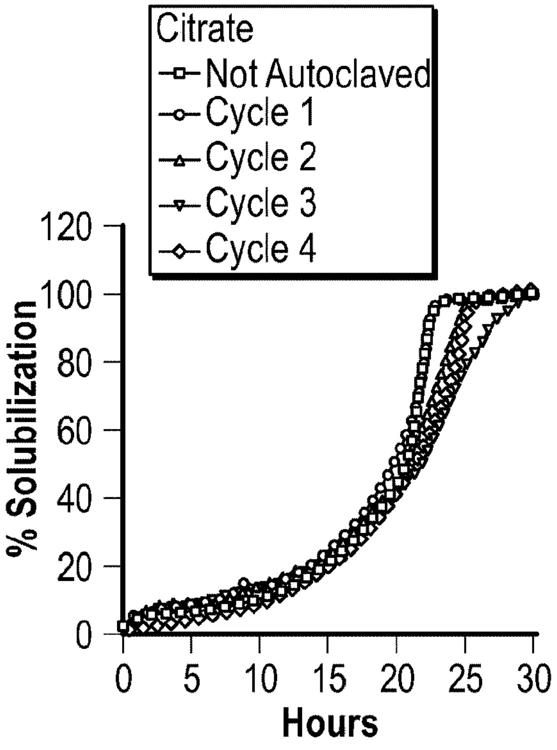
FIGS. 3A-3C show dissolution curves for amino-hydrogel microspheres of Formula 2 ($R^1$=(N,N-dimethylamino) sulfonyl)) at pH 9.4, after 0-4 autoclave cycles in different buffers.
Figure 3B:
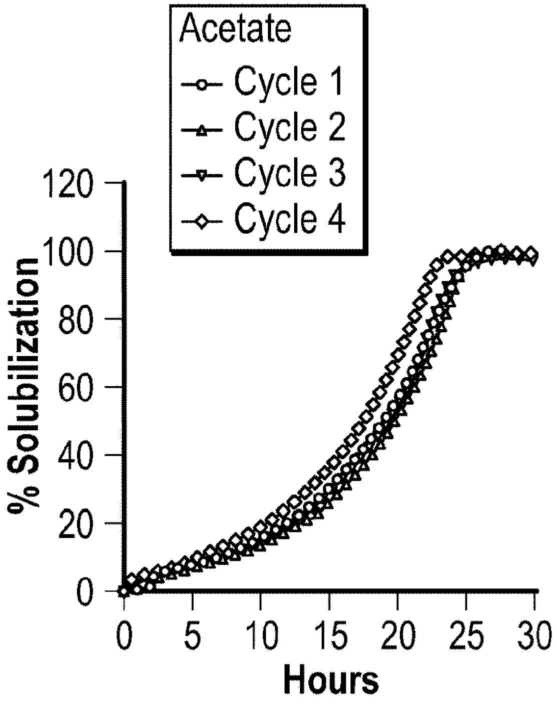
Figure 3C:
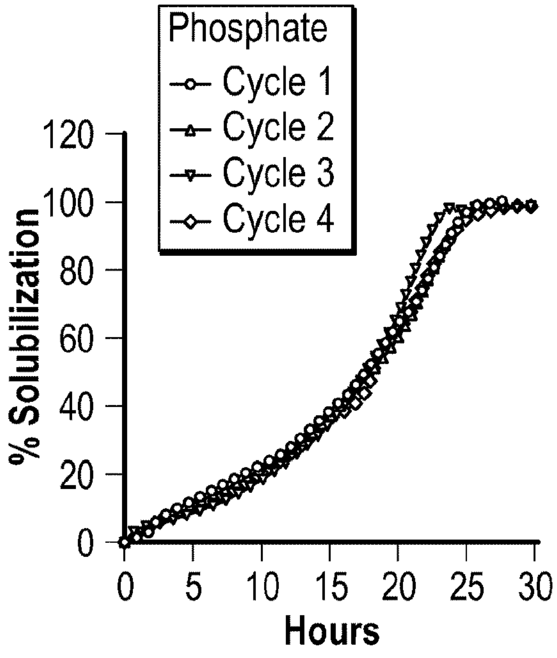

To determine the time to reverse gelation, a 0.5 mL sample of microsphere slurry in a 1.5 mL micro centrifuge tube was washed with 3×1 mL of 100 mM HEPES, pH 7.6, by pelleting at 21,000 g for 5 min. The pellet was treated with 0.020 mL of 10 mM 5-carboxyfluorescein HSE in DMSO for 30 min. The MSs were washed with 3×1 mL water and 3×1 mL 100 mM NaOAc. Microsphere dissolution curves were determined for 0.1 mL samples in 2.5 mL of 100 mM borate buffer, pH 9.4, at 37 °C as reported (Schneider et al., *Bioconj Chem* (2016) 27: 1210). Linear regression was performed on the region where solubilization was between 50% and 95%. The time at 100% solubilization was calculated from the equation: $t_R$G=100-Y intercept/slope. Dissolution curves are shown in FIGS. 3A-3C. The time to reverse gelation was observed to be constant within 7% st. dev. of the mean, similar to the error obtained with 4 replicates of identical samples (8%).

Figure 4:
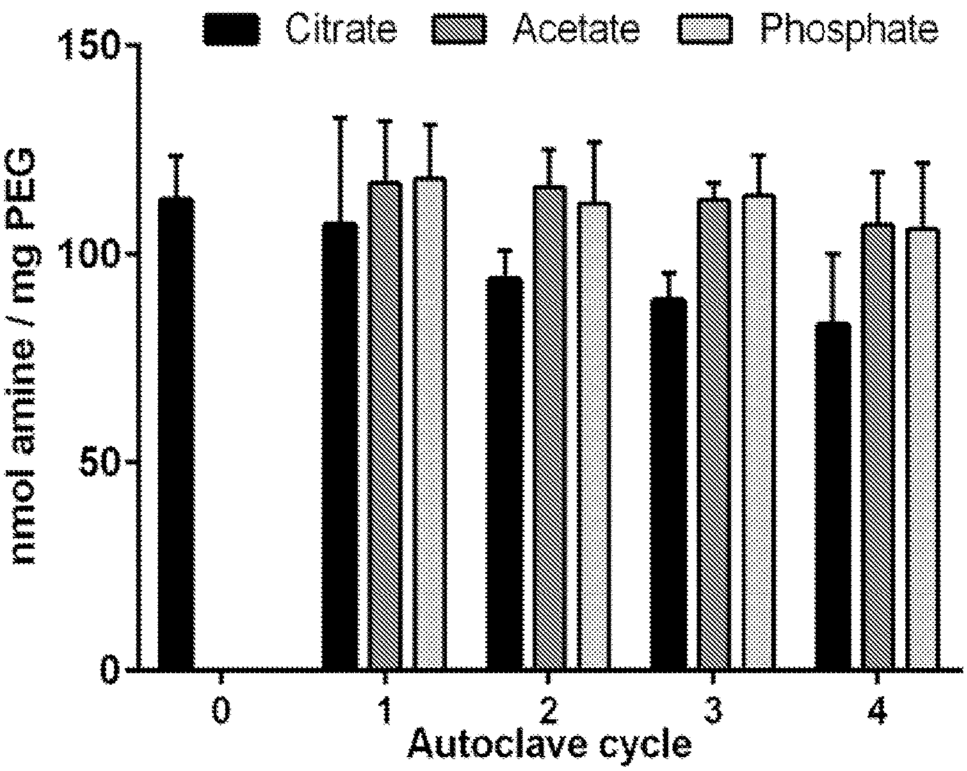
FIG. 4 shows the ratio of free amine groups to PEG for amino-hydrogel microspheres ($R^1$=(N,N-dimethylamino) sulfonyl)) at pH 9.4, after 0-4 autoclave cycles in different buffers.

While the ratio of amine groups to PEG was stable for amino-hydrogel microspheres subjected to autoclaving in phosphate or acetate buffers, a loss of amine groups (~7% per cycle) was observed with citrate buffer. (FIG. 4) This is hypothesized to be due to formation of citric anhydride and subsequent amine citroylation during the autoclave cycle (Chumsae et al., *Anal. Chem.* (2014) 86: 8932.

Sterility of the final amino hydrogel microspheres was demonstrated according to USP 71 guidelines. Autoclaved hydrogels demonstrated no detectable microbial growth.

Example 3

Calculation of Crosslink Loss Due to Hydrogel Exposure to Increased Temperatures One mechanism for degradation of hydrogels comprising beta-eliminative linkers during sterilization by autoclaving is the accelerated loss of crosslinking due to linker cleavage at high temperatures. Other mechanisms may also apply, for example enhanced reactivity of functional groups such as amines at higher temperatures.

The cleavage rate of individual crosslinks at a particular temperature and pH can be estimated through the study of PEG-linker-lysine probes as described in Preparation A, which represent an individual crosslink unit of a hydrogel and can be readily analyzed for cleavage by standard analytical methods such as HPLC. It has been demonstrated that the beta-eliminative cleavage reaction is first-order in hydroxide, and thus the cleavage rate changes 10-fold for each pH unit change according to equation 2 (Santi et al., *Proc. Natl. Acad. Sci. USA* 2011, 109 (16): 6211-6):

$$k_{pH2}=k_{pH1}\cdot 10^{(pH2-pH1)} \quad (2)$$

The temperature dependence of the reaction is described by the Arrhenius equation (equation 3)

$$k=A\cdot e^{(-Ea/RT)} \quad (3)$$

where k is the rate constant ($=\ln(2)/t_{1/2,L2}$), T is the temperature in ° K, A is a preexponential factor, $E_a$ is the activation energy, and R is the universal gas constant. A and $E_a$ are determined experimentally through study of the change in reaction rate as a function of temperature, and then may be used to predict reaction rates at different temperatures. An example of an Arrhenius plot for cleavage of a PEG-linker-lysine having $R^1$=morpholinosulfonyl of Formula 2 with the lysine attached at the epsilon-amine, based on experimental data between 37 and 80 °C is shown in FIG. 5. The data estimate the activation energy $E_a$=117 kJ/mol. Comparable data for $R^1$ as $Me_2N—SO_2$ and 4-($CF_3$)-phenyl-$SO_2$ are shown in Table 3.

TABLE 3

Arrhenius parameters for linker cleavage

| $R^1$ | $t_{1/2}$ (h @ 37° C., pH 7.4) | A ($s^{-1}$) | $E_a$ (kJ/mol) |
|---|---|---|---|
| 4-$CF_3$)-phenyl-$SO_2$ | 14 | $1.9 \times 10^{13}$ | 107.0 |
| Morpholino-$SO_2$ | 400 | $2.5 \times 10^{13}$ | 117.0 |
| $Me_2N—SO_2$ | 1672 | $7.7 \times 10^{13}$ | 123.5 |

While the rate of crosslink cleavage in a hydrogel will increase exponentially with temperature, there is an exponential decrease in cleavage rate as the pH is lowered. By combining equations (2) and (3), the change in pH required to compensate for the rate of linker cleavage due to temperature change from $T_1$ to $T_2$ (in degrees Kelvin) can be calculated by equation (4):

$$\Delta pH = \frac{E_a}{R\cdot\ln(10)}\cdot\left[\frac{1}{T_1}-\frac{1}{T_2}\right] \quad (4)$$

Thus if the stability of a hydrogel comprising beta-eliminative linkers is known at a set of temperature and pH conditions $T_1$ and $pH_1$, it is possible to calculate a pH value $pH_2$ under which that hydrogel is equally stable at temperature $T_2$ if the activation energy $E_a$ for the cleavage reaction is known. As an example, for a hydrogel crosslinked by beta-eliminative linkers wherein $E_a$=117 kJ/mol as described above, if such a hydrogel undergoes a certain amount of crosslink cleavage in 1 hour at pH 7.4 and 37 °C (310.14° K), then the same amount of crosslink cleavage in 1 hour at 121 °C (394.14° K) would be observed at $pH_2$=3.2 (ΔpH=4.2).

This relationship can be used to estimate suitable conditions for the autoclave sterilization of hydrogels comprising beta-eliminative linkers. The rate of cleavage of the cross-linker, and thus the activation energy for that process, is determined by $R^1$ and the nature of the spacer connection as described above. By defining an acceptable level of cross-linker cleavage, for example by setting limits on the variability in the degelation time $t_{RG}$, during the sterilization process, and knowing $E_a$, suitable sterilization pH values can be estimated. From equation (1), the effect on $t_{rg}$ of changing the extent of crosslinking from $f_1$ to $f_2$ in a hydrogel comprised on linkers having individual cleavage half-lives of $t_{1/2,L2}$ is given by equation (5)

$$\Delta t_{rg} = \frac{t_{1/2,L2}}{\ln(2)}\cdot\ln\left[\frac{(1-f_2)}{(1-f_1)}\right] \quad (5)$$

When expressed as a fractional change in $\Delta t_{rg}$ (equation 6):

$$\Delta t_{rg}/t_{rg}=[ln(1-f_2)-ln(1-f_1)]/[ln(1-f_1)-ln(0.39)] \quad (6)$$

Thus, for a perfect hydrogel comprised of 100% initial crosslinks (i.e., $f_1$=0), cleavage of 10% of those crosslinks during sterilization (i.e., $f_2$=0.1) should result in an 11% decrease in $t_{rg}$, disregarding any other structural changes that may occur to the hydrogel during the sterilization process. For an initially imperfect hydrogel, the effect of such a loss in crosslinking on $t_{rg}$ is greater: when $f_1$=0.2, for example, a 10% loss in crosslinking to $f_2$=0.28 results in a 15% change in $t_{rg}$, and when $f_1$=0.3, for example, a 10% loss in cross-linking to $f_2$=0.37 results in a 18% change in $t_{rg}$. If it is desired to maintain the $t_{rg}$ within Conversely, if it is desired to maintain the $t_{rg}$ within a factor of $X=\Delta t_{rg}/t_{rg}$, then the value of $f_2$ must be maintained as in equation (7)

$$f_2<=1-\exp[(1+X)\cdot ln(1-f_1)-X\cdot ln(0.39)] \quad (7)$$

From equation (7), Table 3 shows the maximum allowable loss in crosslinking $\Delta f=f_2-f_1$ that will maintain $\Delta t_{rg}/t_{rg}$ within a given tolerance. From this table, it can be seen that to maintain a tolerance of 5% for $t_{rg}$ will require a loss of less than 4.6% of the crosslinks from a perfect hydrogel ($f_1$=0), and less than 2.8% of the crosslinks from a hydrogel initially having 80% of the theoretical number of crosslinks ($f_1$=0.2).

TABLE 4

Calculated values of Δf for a resulting fractional change in degelation time $\Delta t_{rg}/t_{rg}$ for a hydrogel having an initial fraction of broken crosslinks $f_1$.

| | $\Delta f = f_2 - f_1$ | | | |
|---|---|---|---|---|
| $\Delta t_{rg}/t_{rg}$ | −0.05 | −0.1 | −0.15 | −0.2 |
| $f_1$ | | | | |
| 0 | 0.0460 | 0.0899 | 0.1317 | 0.1717 |
| 0.05 | 0.0414 | 0.0809 | 0.1188 | 0.1550 |
| 0.1 | 0.0369 | 0.0722 | 0.1061 | 0.1386 |
| 0.15 | 0.0325 | 0.0637 | 0.0937 | 0.1226 |
| 0.2 | 0.0282 | 0.0555 | 0.0817 | 0.1071 |
| 0.25 | 0.0241 | 0.0475 | 0.0701 | 0.0919 |
| 0.3 | 0.0202 | 0.0398 | 0.0588 | 0.0773 |
| 0.35 | 0.0164 | 0.0324 | 0.0479 | 0.0631 |
| 0.4 | 0.0128 | 0.0253 | 0.0375 | 0.0495 |

Knowing the maximum allowable extent of crosslink cleavage during sterilization, the required buffer pH for autoclaving can be estimated based on the rate of individual linker cleavage under the sterilization conditions of temperature and time, using the Arrhenius relationship in equation (3). For example, a crosslinker having $R^1$=morpholinosulfonyl (cleavage $t_{1/2}$=400 h at pH 7.4, 37 °C) and having the Arrhenius relationship shown in FIG. 1 is predicted to have a cleavage $t_{1/2}$=0.025 h (k=28 $h^{-1}$) at pH 7.4, 121 °C. As crosslink cleavage is a first-order reaction, the fraction of crosslinks cleaved over time period T is given as 1−exp(−kT). Sterilization at 121 °C, pH 7.4, for 20 min would thus result in essentially complete destruction of the hydrogel to monomeric units (99.99% crosslink cleavage). At pH 5, however, the reaction is slowed 251-fold such that only 3.6% of the crosslinks will be cleaved, and at pH 4 only 0.4% will be cleaved. From Table 3 it can be seen that pH 5 would give satisfactory results in terms of keeping $t_{rg}$ within 10% for hydrogels of initial quality down to $f_1$=0.3, whereas pH 4 is expected to give satisfactory results for all hydrogels within a 5% tolerance of $t_{rg}$. In practice, the hydrogels are exposed to elevated temperatures for longer times due to the requirement for a slow cooling period, and a conservative estimate wherein the hydrogel is kept at sterilizing temperature (121 °C) for a full hour estimates that pH 4 would give 1.1% cleavage, again suitable for maintaining a 5% tolerance in $t_{rg}$.

Example 5

Preparation of Degradable PEG-Hydrogels

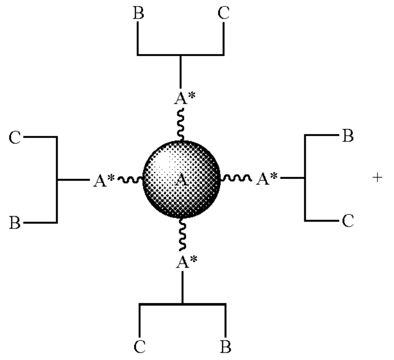

1st prepolymer

-continued

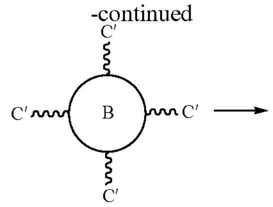

1st prepolymer

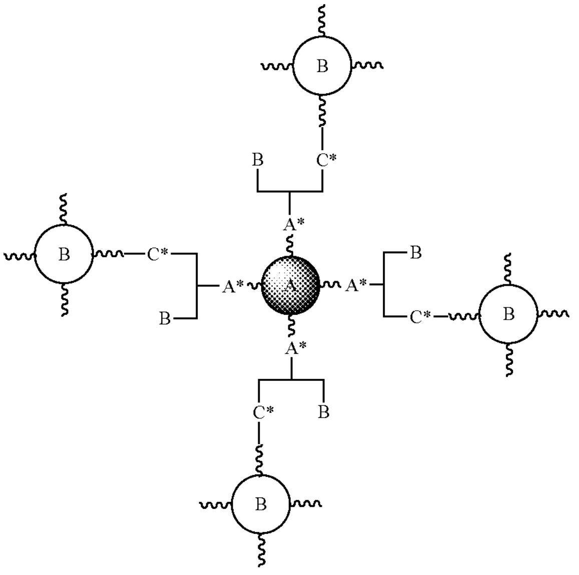

hydrogel

Hydrogels of the invention are prepared by polymerization of two prepolymers comprising groups C and C' that react to form a connecting functional group, C*. The prepolymer connection to one of C or C' further comprises a cleavable linker introduced by reaction with a molecule of Formula (3), so as to introduce the cleavable linker into each crosslink of the hydrogel.

In one embodiment, a first prepolymer comprises a 4-armed PEG wherein each arm is terminated with an adapter unit having two mutually-unreactive ("orthogonal") functional groups B and C. B and C may be initially present in protected form to allow selective chemistry in subsequent steps. In certain embodiments, the adapter unit is a derivative of an amino acid, particularly lysine, cysteine, aspartate, or glutamate, including derivatives wherein the alpha-amine group has been converted to an azide, for example monoesters of 2-azidoglutaric acid. The adapter unit is connected to each first prepolymer arm through a connecting functional group A*, formed by condensation of a functional group A on each prepolymer arm with cognate functional group A' on the adapter unit. A second prepolymer comprises a 4-armed PEG wherein each arm is terminated with a functional group C' having complimentary reactivity with group C of the first prepolymer, such that crosslinking between the two prepolymers occurs when C and C' react to form C*.

As an illustrative example, a first prepolymer was prepared as follows. H-Lys(Boc)-OH was acylated with a linker of Formula 3 wherein Z=azide to give an adapter unit where A=COOH, B=Boc-protected $NH_2$, and C=azide. This was coupled to 20-kDa 4-armed PEG-tetraamine, and the Boc group was removed to provide a first prepolymer wherein A*=amide, B=$NH_2$, and C=azide and wherein a cleavable linker of formula 3 is incorporated into the linkage between each arm and group C of the first prepolymer. The corresponding second prepolymer was prepared by acylation of 20-kDa 4-armed PEG-tetraamine with 5-cyclooctynyl succinimidyl carbonate to give a second prepolymer wherein C'=cyclooctyne. Upon mixing of the first and second prepolymers, reaction of the C=azide and C'=cyclooctyne groups form corresponding triazole groups and thereby crosslink the two prepolymers into a 3-dimensional network, with each crosslink comprising a cleavage linker resulting from incorporation of the compound of Formula 3, and wherein each node resulting from incorporation of a first prepolymer comprises a remaining functional group B=$NH_2$ which can be derivatized for attachment of further linkers, drugs, fluorophores, metal chelators, and the like.

Prepolymer A Wherein A*=Amide, B=Amine, and C=Azide

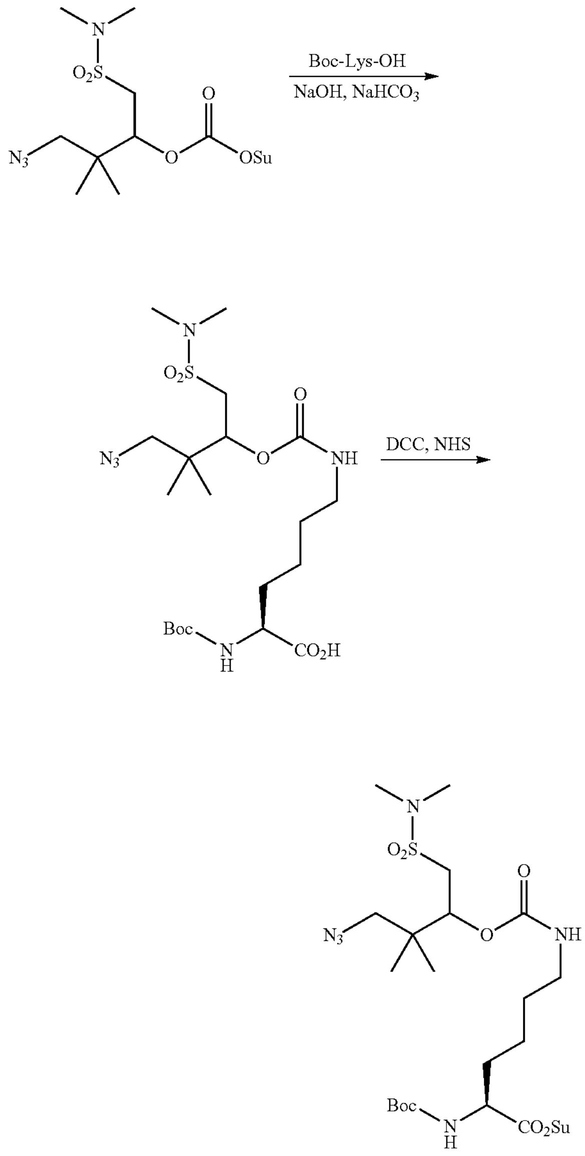

-continued

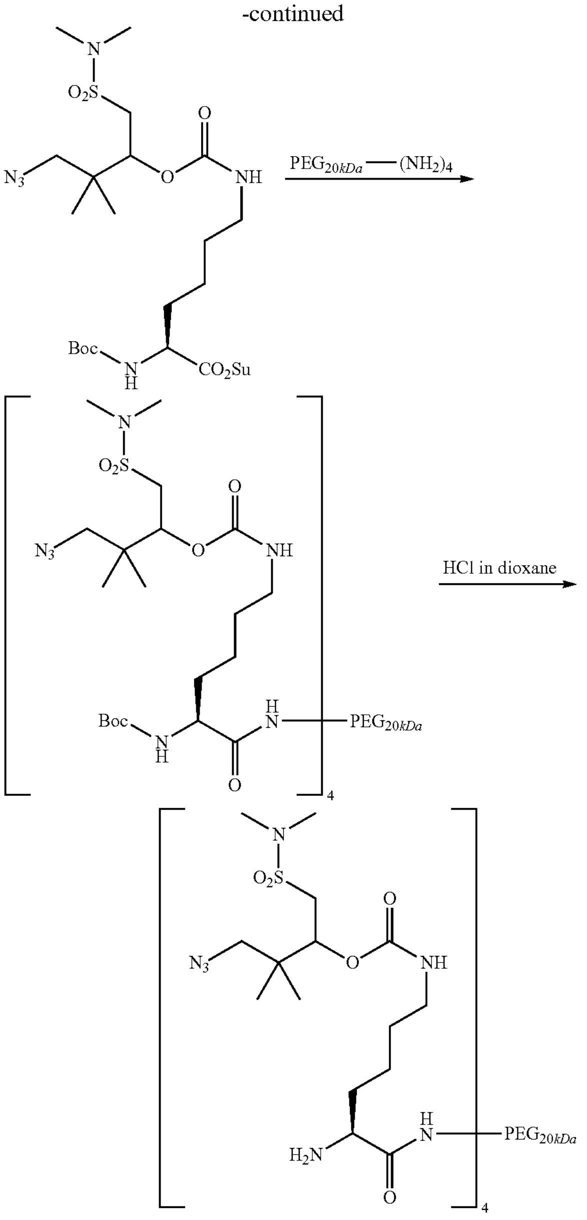

(1) $N^{\alpha}$-Boc-$N^{\varepsilon}$-{4-Azido-3,3-dimethyl-1-[(N,N-dimethyl)aminosulfonyl]-2-butyloxycarbonyl}-Lys-OH A solution of Boc-Lys-OH (2.96 g, 12.0 mmol) in 28 mL of $H_2O$ was successively treated with 1 M aq NaOH (12.0 mL, 12.0 mmol), 1 M aq $NaHCO_3$ (10.0 mL, 10.0 mmol), and a solution of O-{4-azido-3,3-dimethyl-1-[(N,N-dimethyl)aminosulfonyl]-2-butyl}-O'-succinimidyl carbonate (3.91 g, 10.0 mmol, 0.1 M final concentration) in 50 mL of MeCN. After stirring for 2 h at ambient temperature, the reaction was judged to be complete by C18 HPLC (ELSD). The reaction was quenched with 30 mL of 1 M $KHSO_4$ (aq). The mixture was partitioned between 500 mL of 1:1 EtOAc:$H_2O$. The aqueous phase was extracted with 100 mL of EtOAc. The combined organic phase was washed with $H_2O$ and brine (100 mL each) then dried over $MgSO_4$, filtered, and concentrated by rotary evaporation to provide the crude title compound (5.22 g, 9.99 mmol, 99.9% crude yield) as a white foam.

C18 HPLC, purity was determined by ELSD: 99.1% (RV=9.29 mL).

LC-MS (m/z): calc, 521.2; obsd, 521.3 $[M-H]^-$.

(2) $N^{\alpha}$-Boc-$N^{\varepsilon}$-{4-Azido-3,3-dimethyl-1-[(N,N-dimethyl)aminosulfonyl]-2-butyloxycarbonyl}-Lys-OSu. Dicyclohexylcarbodiimide (60% in xylenes, 2.6 M, 4.90 mL, 12.7 mmol) was added to a solution of $N^{\alpha}$-Boc-$N^{\varepsilon}$-{4-azido-3,3-dimethyl-1-[(N,N-dimethyl)aminosulfonyl]-2-butyloxycarbonyl}-Lys-OH (5.11 g, 9.79 mmol, 0.1 M final concentration) and N-hydroxysuccinimide (1.46 g, 12.7 mmol) in 98 mL of $CH_2Cl_2$. The reaction suspension was stirred at ambient temperature and monitored by C18 HPLC (ELSD). After 2.5 h, the reaction mixture was filtered, and the filtrate was loaded onto a SiliaSep 120 g column. Product was eluted with a step-wise gradient of acetone in hexane (0%, 20%, 30%, 40%, 50%, 60%, 240 mL each). Clean product-containing fractions were combined and concentrated to provide the title compound (4.95 g, 7.99 mmol, 81.6% yield) as a white foam.

C18 HPLC, purity was determined by ELSD: 99.7% (RV=10.23 mL).

LC-MS (m/z): calc, 520.2; obsd, 520.2 $[M+H-Boc]^+$.

(3) ($N^{\alpha}$-Boc-$N^{\varepsilon}$-{4-Azido-3,3-dimethyl-1-[(N,N-dimethyl)aminosulfonyl]-2-butyloxycarbonyl}-LyS)$_4$-$PEG_{20kDa}$ $PEG_{20kDa}$-$(NH)_4$ (20.08 g, 0.9996 mmol, 3.998 mmol $NH_2$, 0.02 M $NH_2$ final concentration) was dissolved in 145 mL of MeCN. A solution of $N^{\alpha}$-Boc-$N^{\varepsilon}$-{4-azido-3,3-dimethyl-1-[(N, N-dimethyl)aminosulfonyl]-2-butyloxycarbonyl}-Lys-OSu (2.976 g, 4.798 mmol) in 50 mL of MeCN was added. The reaction was stirred at ambient temperature and analyzed by C18 HPLC (ELSD). The starting material was converted to a single product peak via three slower eluting intermediate peaks. After 1 h, $Ac_2O$ (0.37 mL, 4.0 mmol) was added. The reaction mixture was stirred 30 min more then concentrated to ~50 mL by rotary evaporation. The reaction concentrate was added to 400 mL of stirred MTBE. The mixture was stirred at ambient temperature for 30 min then decanted. MTBE (400 mL) was added to the wet solid, and the suspension was stirred for 5 min and decanted. The solid was transferred to a vacuum filter, and washed/triturated with 3×100 mL of MTBE. After drying on the filter for 10 min, the solid was transferred to a tared 250 mL HDPE packaging bottle. Residual volatiles were removed under high vacuum until the weight stabilized to provide the title compound (21.23 g, 0.9602 mmol, 96.1% yield) as a white solid.

C18 HPLC, purity was determined by ELSD: 89.1% (RV=10.38 mL) with a 10.6% impurity (RV=10.08).

(4) ($N^{\varepsilon}$-{4-Azido-3,3-dimethyl-1-[(N,N-dimethyl)aminosulfonyl]-2-butyloxycarbonyl}-Lys)$_4$-$PEG_{20kDa}$ ($N^{\varepsilon}$-{4-Azido-3,3-dimethyl-1-[(N,N-dimethyl)aminosulfonyl]-2-butyloxycarbonyl}-Lys)$_4$-$PEG_{20kDa}$ (19.00 g, 0.8594 mmol, 3.438 mmol Boc, 0.02 M Boc final concentration) was dissolved in 86 mL of 1,4-dioxane. After stirring for 5 min to fully dissolve the PEG, 4 M HCl in dioxane (86 mL, 344 mmol HCl) was added. The reaction was stirred at ambient temperature and analyzed by C18 HPLC (ELSD). The starting material was converted to a single product peak via three faster eluting intermediate peaks. After 2 h, the reaction mixture was concentrated to ~40 mL. THF (10 mL) was added to the concentrate, and the solution was again concentrated to ~40 mL. The viscous oil was poured into 400 mL of stirred $Et_2O$. After stirring at ambient temperature for 20 min, the supernatant was decanted from the precipitate. The wet solid was transferred to a vacuum filter with the aid of 200 mL $Et_2O$ and washed with $Et_2O$ (3×75 mL). The solid was dried on the filter for 10 min then transferred to a tared 250 mL HDPE packaging bottle. Residual volatiles were removed under high vacuum overnight to provide the title compound (17.52 g, 0.8019 mmol, 93.3% yield @ 4 HCl) as a white solid.

C18 HPLC, purity was determined by ELSD: 99.2% (RV=9.34 mL).

Prepolymer B Wherein C'=Cyclooctynyl

A 4-mL, screw top vial was charged with $PEG_{20kDa}$-$[NH_2]_4$ (SunBright PTE-200PA; 150 mg, 7.6 μmol PEG, 30.2 μmol $NH_2$, 1.0 equiv, 20 mM final amine concentration), MeCN (1.5 mL), and $iPr_2NEt$ (7 μL, 40 μmol, 1.3 equiv, 27 mM final concentration). A solution of the activated ester cyclooctyne (39 μmol, 1.3 equiv, 27 mM final concentration) was added and the reaction mixture was stirred at ambient temperature. Reactions were monitored by C18 HPLC (20-80% B over 11 min) by ELSD. When complete, $Ac_2O$ (3 μL, 30 μmol, 1 equiv per starting $NH_2$) was added to the reaction mixture and the mixture was stirred for 30 min. The reaction mixture was then concentrated to a thick oil and suspended in MTBE (20 mL). The resulting suspension as vigorously stirred for 10 min. The resulting solids were triturated three times with MTBE (20 mL) by vigorously mixing, pelleting in a centrifuge (2800 rpm, 4 °C, 10 min), and removal of the supernatant by pipette. The resulting solids were dried under vacuum at ambient temperature for no more than 30 min. Stock solutions were prepared in 20 mM NaOAc (pH 5) with a target amine concentration of 20 mM. Cyclooctyne concentration was then verified by treatment with $PEG_7$-$N_3$ (2 equiv) and back-titration of the unreacted $PEG_7$-$N_3$ with DBCO—$CO_2H$.

Macromonomers prepared using this procedure include those wherein the cyclooctyne group is MFCO, 5-hydroxycyclooctyne, 3-hydroxycyclooctyne, BCN (bicyclo[6.1.0]non-4-yn-9-ylmethyl), DIBO, 3-(carboxymethoxy)cyclooctyne, and 3-(2-hydroxyethoxy)cyclooctyne, prepared using MFCO pentafluorophenyl ester, 5-((4-nitrophenoxy-carbonyl)oxy)cyclooctyne, 3-(4-nitrophenoxycarbonyl)oxycyclooctyne, BCN hydroxysuccinimidyl carbonate, DIBO 4-nitrophenyl carbonate, 3-(carboxymethoxy)cyclooctyne succinimidyl ester, and 3-(hydroxyethoxy)cyclooctyne 4-nitrophenyl carbonate, respectively.

Hydrogel Microsphere preparation. Hydrogel microspheres were prepared and activated as described in Schneider et al. (2016) Bioconjugate Chemistry 27: 1210-15.

Example 6

Preparation of a Sterile Hydrogel Conjugate

The sterilized hydrogels of the invention may be used for the preparation of sterile hydrogel-drug conjugates suitable for in vivo administration by attachment of small molecule, peptide, protein, or nucleic acid drugs as described, for example, in PCT Application US2020/026726 (filed 3 Apr. 2020), and U.S. Pat. No. 9,649,385. In general, the method of making sterile hydrogel conjugates comprises three steps: (1) sterilization of hydrogel microspheres; (2) activation of the hydrogel micro spheres for conjugation; and (3) conjugation. Standard procedures for steps (2) and (3) under non-aseptic conditions have been previously described (see, for example Schneider et al. (2016) Bioconjugate Chemistry 27: 1210-15). In the present invention, these methods have been adapted for aseptic processing by conducting them in a closed, sterile sieve-bottom stirred washer/reactor (see Henise et al. (2020), Engineering Reports. 2020; e12213. https://doi.org/10.1002/eng2.12213) where all liquids are introduced through appropriate sterilizing filters. For Step (1), a hydrogel microsphere slurry in the appropriate buffer, for example acetate or phosphate buffer at pH 2-5, is placed into the washer/reactor, which is then closed with the sterilizing filters and autoclaved according to the methods of the invention. The suspension is allowed to cool to ambient temperature, and the sterilization buffer is removed by draining through the sieve bottom. The resulting sterile microsphere slurry is then washed with sterile buffer or water and exchanged into an appropriate solvent for the activation step. In Step (2), the sterile microsphere slurry in organic solvent is treated with an activating agent and any neutralizing base that is required for attachment of the activating group. All reagents are introduced into the washer/reactor through the appropriate sterilizing filters, and excess reagents are removed at the end of the reaction through the sieve bottom. For Step (3), the sterile activated hydrogel microspheres are suspended in an appropriate loading buffer, selected on the basis of solubility and stability of the linker-drug to be conjugated, and a solution of the linker-drug is introduced through the appropriate sterile filters. If necessary, the conjugation reaction may be performed at elevated temperature by heating the washer/reactor, or at lower than ambient temperatures by chilling. Once the conjugation is complete, excess reagents are removed through the sieve bottom and the sterile microsphere conjugate is exchanged into an appropriate storage or administration formulation.

Example 7

Preparation of a Sterile Hydrogel-Exenatide Conjugate

To illustrate the use of the sterilized hydrogels of the invention, a sterile conjugate of the exenatide peptide derivative [$Gln^{28}$]exenatide to hydrogel microspheres was prepared.

(1) Preparation of the linker-drug, $N^{\alpha}$-{4-azido-3,3-dimethyl-1-[(N,N-dimethyl)amino-sulfonyl]-2-butyloxycarbonyl}-[$Gln^{28}$]exenatide, has been described in PCT Application US/2020/026726 (filed 3 Apr. 2020; incorporated herein by reference). In a 25 ml fritted SPE column, protected [$Gln^{28}$]exenatide (fmoc α-amine) on rink amide resin (0.63 meq/g substitution, 0.12 mmol peptide/g peptide-resin, 1.00 g peptide-resin, 0.12 mmol peptide) was swollen in 10 ml of DMF for 30 min at ambient temperature. DMF was removed by syringe filtration using a f/f Luer adapter and a 12 ml syringe, and the swollen resin was treated with 5% 4-methylpiperidine in DMF (2×10 ml, 5 min each; then 2×10 ml, 20 min each). The fmoc-deprotected resin was then washed with DMF (10×10 ml), and supernatants were removed by syringe filtration. The washed resin was suspended in 8.4 ml DMF and treated with 3.6 ml of 4-azido-3,3-dimethyl-1-[(N,N-dimethyl)aminosulfonyl]-2-butyl succinimidyl carbonate (0.10 m in DMF, 0.36 mmol, 30 mm final concentration) and 4-methylmorpholine (40 μl, 0.36 mmol, 30 mm final concentration). The reaction mixture was agitated using an orbital shaker. After 20 h, the supernatant was removed by syringe filtration, and the resin was washed with successively DMF (5×15 ml) and $CH_2Cl_2$ (5×15 ml). Kaiser test was negative for free amines in the intermediate linker-modified resin. The resin was then treated with 10 ml of precooled (0 °C) 90:5:5 trifluoroacetic acid:triisopropylsilane:$H_2O$ while gently agitating on an orbital shaker. After 2 h, the resin was vacuum filtered and washed with TFA (2×1.5 ml). The filtrate was concentrated by rotary evaporation to ~6 ml. The crude linker-peptide was precipitated by dropwise addition of the TFA concentrate to 40 ml of −20 °C MTBE in a tared 50 ml Falcon tube. After incubating at −20 °C for 10 min, the crude linker-peptide suspension was pelleted by centrifugation (3000×g, 2 min, 4 °C), and the supernatant was decanted. The resulting pellet was suspended in 40 ml of −20 °C MTBE, vortexed to mix, centrifuged, and decanted as above. After drying under high vacuum, the pellet was isolated as an off-white solid (575 mg) that was then dissolved in 8 ml of 5% acetic acid (~70 mg/ml). After heating in a 50 °C water bath for 45 min, the solution was purified by preparative C18 HPLC to provide 13 ml of the title compound (3.33 mm, 43 μmol by $A_{280}$) as an aqueous solution. Lyophilization provided 235 mg of a white solid. $C_{18}$ HPLC purity determined at 280 nm: 90.0% (Rv=11.47 ml). $M_{av}$: 4476.9 calc; 4476 obsd.

(2) Hydrogel microspheres of Formula (2) wherein $R^1$=$SO_2NMe_2$ were prepared as described above in Example 5. The hydrogel microspheres were suspended in 0.1 M acetate buffer, pH 4.0, placed in the washer/reactor, and steam sterilized in the autoclave at 121 °C with a hold time of 20 min.

(3) The buffer was drained from the sterile hydrogel microsphere suspension through the sieve bottom of the washer/reactor, and the microspheres were exchanged into acetonitrile introduced through a sterile filter. Solutions of BCN succinimidyl carbonate (26 mM, 1.2 equivalents/equivalent of microsphere amine) and triethylamine (172 mM, 4 equivalents/equivalent of microsphere amine) in acetonitrile were added through sterilizing filters, and the mixture was stirred gently for 3 h. Excess reagents were drained through the sieve bottom of the washer/reactor, and the microspheres were washed with acetonitrile introduced through a sterile filter, followed by washing and resuspension into 50% 0.1 M citrate, pH 3.5, 50% isopropanol, 30 mM methionine loading buffer.

(4) A solution of the linker-drug in loading buffer (24 mM, 1.1 molar equivalents/equivalent of microsphere amine) was introduced by sterile filter, and the mixture was stirred with gentle warming to 40 °C for 21 h. Excess reagents were drained through the sieve bottom of the washer/reactor, and the microspheres were washed with IPA/citrate/methionine buffer providing a sterile suspension of [$Gln^{28}$]exenatide-loaded hydrogel microspheres. Analysis of the resulting microspheres indicated a drug content of 4.2±0.2 nmol of peptide/mg of microsphere slurry.

The invention claimed is:

1. A method to sterilize a hydrogel linked with a cross-linker that degrades by beta elimination, which method comprises heating said hydrogel at a temperature of up to about 121 °C for up to 1 hour in a medium having a pH of between 2 and 4.

2. The method of claim 1 wherein the medium comprises a non-reactive buffer.

3. The method of claim 2 wherein said buffer is phosphate or acetate buffer.

4. The method of claim 1 wherein the heating said hydrogel at a temperature of up to about 121 °C for up to 1 hour in a medium having a pH of between 2 and 4 comprises adjusting the pH of the medium containing said crosslinked hydrogel to a pH of between 3 and 4.

5. The method of claim 1 wherein the rate of degradation by beta elimination is controlled by one or more substituents contained in the cross-linker.

6. The method of claim 5 wherein the hydrogel comprises a cross-linker of the formula:

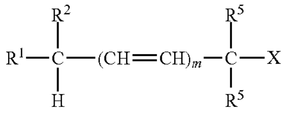

wherein m is 0 or 1;

X comprises a functional group connecting the cross-linker to a first polymer;

at least one of $R^1$, $R^2$, and $R^5$ comprises a functional group Z connecting the crosslinker to a second polymer;

wherein one and only one of $R^1$ and $R^2$ may be H or may be alkyl, arylalkyl or heteroarylalkyl, each optionally substituted;

at least one or both $R^1$ and $R^2$ is independently CN; $NO_2$;

optionally substituted aryl;

optionally substituted heteroaryl;

optionally substituted alkenyl;

optionally substituted alkynyl;

$COR^3$ or $SOR^3$ or $SO_2R^3$ wherein $R^3$ is H or optionally substituted alkyl;

aryl or arylalkyl, each optionally substituted;

heteroaryl or heteroarylalkyl, each optionally substituted; or $OR^9$ or $NR^9_2$ wherein each $R^9$ is independently H or optionally substituted alkyl, or both $R^9$ groups taken together with the nitrogen to which they are attached form a heterocyclic ring;

$SR^4$ wherein $R^4$ is optionally substituted alkyl;

aryl or arylalkyl, each optionally substituted; or heteroaryl or heteroarylalkyl, each optionally substituted; and each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted;

or

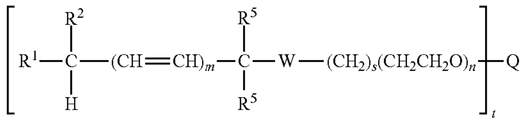

wherein m is 0 or 1;

n is 1-1000;

s is 0-2;

t is 2, 4, 8, 16 or 32;

W is O(C=O)O, O(C=O)NH, O(C=O)S, or

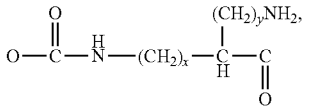

wherein x and y=0-4;

Q is a core group having a valency=t;

wherein at least one of $R^1$, $R^2$, and $R^5$ comprises a functional group $Z^1$ capable of connecting to a polymer, and at least one or both $R^1$ and $R^2$ is independently CN; $NO_2$;

optionally substituted aryl;

optionally substituted heteroaryl;

optionally substituted alkenyl;

optionally substituted alkynyl;

$COR^3$ or $SOR^3$ or $SO_2R^3$ wherein $R^3$ is H or optionally substituted alkyl;

aryl or arylalkyl, each optionally substituted;

heteroaryl or heteroarylalkyl, each optionally substituted; or $OR^9$ or $NR^9_2$ wherein each $R^9$ is independently H or optionally substituted alkyl, or both $R^9$ groups taken together with the nitrogen to which they are attached form a heterocyclic ring;

$SR^4$ wherein $R^4$ is optionally substituted alkyl;

aryl or arylalkyl, each optionally substituted; or heteroaryl or heteroarylalkyl, each optionally substituted; and wherein one and only one of $R^1$ and $R^2$ may be H or may be alkyl, arylalkyl or heteroarylalkyl, each optionally substituted; and each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted.

7. The method of claim 6 wherein X is a carbamate and Z is a triazole, carboxamide, or carbamate.

8. The method of claim 6 wherein the hydrogel comprises a cross-linker of the formula:

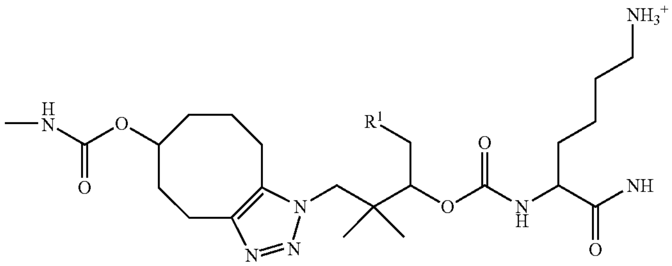

or

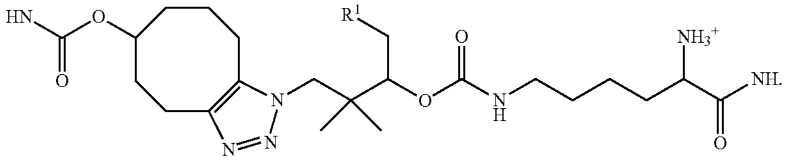

9. The method of claim 8, wherein $R^1$ is CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^{92}$ wherein each $R^9$ is independently H or optionally substituted alkyl, or both $R^9$ groups taken together with the nitrogen to which they are attached form a heterocyclic ring;
$SR^4$ wherein
$R^4$ is optionally substituted alkyl;
aryl or arylalkyl, each optionally substituted; or
heteroaryl or heteroarylalkyl, each optionally substituted.

10. The method of claim 8 wherein $R^1$ is CN or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^{92}$ wherein each $R^9$ is independently H or optionally substituted alkyl, or both $R^9$ groups taken together with the nitrogen to which they are attached form a heterocyclic ring.

11. The method of claim 8 wherein $R^1$ is CN; $SO_2Me$; $SO_2NMe_2$; $SO_2N(CH_2CH_2)_2X$ or $SO_2(Ph\text{-}R^{10})$, wherein X is absent, O, or CH—$R^{10}$ and $R^{10}$ is H, alkyl, alkoxy, $NO_2$, or halogen.

12. The method of claim 1, wherein sterilization is achieved by heating to 121 °C with a hold time of 20 minutes.

13. A hydrogel comprising a cross-linker degradable by a beta-elimination mechanism that has been sterilized by heating the hydrogel at a temperature up to about 121 °C in a medium having a pH between 2 and 4.

14. The hydrogel of claim 13 that is a suspension of microparticles.

15. The hydrogel of claim 13 wherein the cross-linker degradable by a beta-elimination mechanism has the formula

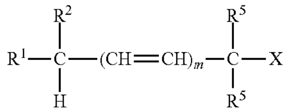

wherein
m is 0 or 1;
X comprises a functional group connecting the cross-linker to a first polymer;
wherein at least one of $R^1$, $R^2$, and $R^5$ comprises a functional group Z connecting the crosslinker to a second polymer;
wherein one and only one of $R^1$ and $R^2$ may be H or may be alkyl, arylalkyl or heteroarylalkyl, each optionally substituted;
at least one or both $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9_2$ wherein each $R^9$ is independently H or optionally substituted alkyl, or both $R^9$ groups taken together with the nitrogen to which they are attached form a heterocyclic ring;
$SR^4$ wherein
$R^4$ is optionally substituted alkyl;
aryl or arylalkyl, each optionally substituted; or
heteroaryl or heteroarylalkyl, each optionally substituted; and
each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted;
or

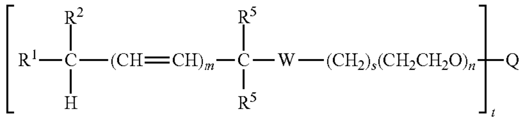

wherein m is 0 or 1;

n is 1-1000;

s is 0-2;

t is 2, 4, 8, 16 or 32;

W is O(C═O)O, O(C═O)NH, O(C═O)S, or

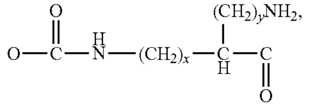

wherein x and y=0-4;

Q is a core group having a valency=t;

wherein at least one of $R^1$, $R^2$, and $R^5$ comprises a functional group Z connecting the crosslinker to a second polymer, and at least one or both $R^1$ and $R^2$ is independently CN; $NO_2$;

optionally substituted aryl;

optionally substituted heteroaryl;

optionally substituted alkenyl;

optionally substituted alkynyl;

$COR^3$ or $SOR^3$ or $SO_2R^3$ wherein $R^3$ is H or optionally substituted alkyl;

aryl or arylalkyl, each optionally substituted;

heteroaryl or heteroarylalkyl, each optionally substituted; or $OR^9$ or $NR^9_2$ wherein each $R^9$ is independently H or optionally substituted alkyl, or both $R^9$ groups taken together with the nitrogen to which they are attached form a heterocyclic ring;

$SR^4$ wherein $R^4$ is optionally substituted alkyl;

aryl or arylalkyl, each optionally substituted; or heteroaryl or heteroarylalkyl, each optionally substituted; and wherein one and only one of $R^1$ and $R^2$ may be H or may be alkyl, arylalkyl or heteroarylalkyl, each optionally substituted; and each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted.

16. The hydrogel of claim 15 wherein m=0, $R^2$ is H, one $R^5$ is H and the other is $C(Me)_2(CH_2)_nZ$ wherein n=0-6, and W is

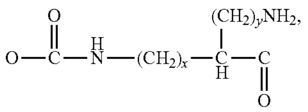

wherein x and y=0-4.

17. The hydrogel of claim 15 wherein the hydrogel comprises a cross-linker of the formula:

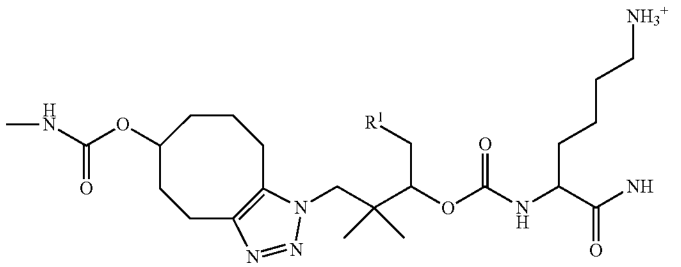

or

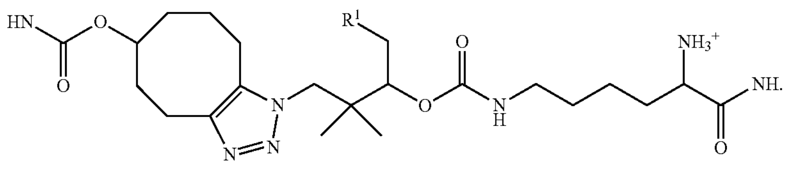

18. The hydrogel of claim 13, wherein the cross-linker has been sterilized by adjusting the medium to a pH between 3 and 4, and heating at a temperature up to about 121 °C.

19. The method of claim 1, wherein a change in reverse gelation time ($t_{RG}$) of the hydrogel after sterilization of the hydrogel is within 20% of an initial value of $t_{RG}$ of the hydrogel before sterilization of the hydrogel.

20. The hydrogel of claim 13, wherein a change in reverse gelation time ($t_{RG}$) of the hydrogel after sterilization of the hydrogel is within 20% of an initial value of $t_{RG}$ of the hydrogel before sterilization of the hydrogel.

* * * * *